United States Patent [19]

Summerton et al.

[11] Patent Number: 5,217,866
[45] Date of Patent: Jun. 8, 1993

[54] POLYNUCLEOTIDE ASSAY REAGENT AND METHOD

[75] Inventors: James Summerton; Dwight Weller, both of Corrvallis, Oreg.

[73] Assignee: Anti-Gene Development Group, Corvallis, Oreg.

[21] Appl. No.: 944,707

[22] Filed: Dec. 18, 1986

Related U.S. Application Data

[63] Continuation-in-part of Ser. No. 712,396, Mar. 15, 1985, and a continuation-in-part of Ser. No. 907,842, Sep. 10, 1986, and a continuation-in-part of Ser. No. 911,258, Sep. 24, 1986.

[51] Int. Cl.$^5$ ............................................. C12Q 1/68
[52] U.S. Cl. ...................................... 435/6; 436/501; 935/77; 935/78
[58] Field of Search ............... 435/6, 91, 172.3, 968; 544/118, 122, 123; 528/391, 403, 405, 406; 436/501, 518, 530, 531, 800, 56; 935/78, 77

[56] References Cited

U.S. PATENT DOCUMENTS

| | | | |
|---|---|---|---|
| 4,166,105 | 8/1979 | Hirschfield | 424/8 |
| 4,362,531 | 12/1982 | de Steenwinkel et al. | 424/12 |
| 4,395,486 | 7/1983 | Wilson et al. | 435/6 |
| 4,430,496 | 2/1984 | Abbott | 536/27 |
| 4,469,863 | 9/1984 | Ts'o et al. | 536/27 |
| 4,486,539 | 12/1984 | Ranki et al. | 436/504 |
| 4,507,433 | 3/1985 | Miller et al. | 525/54.11 |
| 4,558,047 | 12/1985 | Takaya et al. | 514/229 |
| 4,749,647 | 6/1988 | Thomas et al. | 436/504 |
| 4,757,055 | 7/1988 | Miller et al. | 514/44 |
| 4,775,619 | 10/1988 | Urdea | 435/6 |
| 5,034,506 | 7/1991 | Summerton et al. | 528/391 |

FOREIGN PATENT DOCUMENTS 9118898 6/1990 Japan.

OTHER PUBLICATIONS

Manning et al., Biochemistry 16, (7), 1977, pp. 1364–1370.

Lehninger, "Biochemistry", Worth Publishers, Inc. (1972) p. 130.

Serwer, Biosis Abstract No. 67077493, J. of Ultrastructure Research, 65(2), 1978, pp. 112–118.

Nucleic Acids Research, vol. 12, No. 8, issued Apr. 25, 1984 M. Renz et al., "A Colorimetric Method for DNA Hybridazation", see p. 3435.

Akira Murakami et al., "Characterization of Sequence-Specific Oligodeoxy-Biochemistry" 1985, 24, 4041–4046.

Paul S. Miller et al., "Biochemical and Biological Effects of Nonionic Nucleic Acid Methylphosphonates" Biochemistry 1981 20, 1874–1880 Mar. 31, 1981 0006-2960/81/0420-1874$01.25/0 copyrighted 1981 American Chemical Society.

Paul S. Miller et al., "Oligothymidylate Analogues Having Stereoregular, Alternating Methyphosphonate/Phosphodiester Backbones" Synthesis nd Physical Studies. The Journal of Biological Chemistry pp. 9659–9665. 1980.

(List continued on next page.)

Primary Examiner—Amelia Burgess Yarbrough
Attorney, Agent, or Firm—Peter J. Dehlinger; Gary R. Fabian

[57] ABSTRACT

A diagnostic reagent and system for determination of a single-stranded polynucleotide analyte having a selected target sequence. The reagent includes a solid support and multiple support-bound polymers designed to bind specifically to the analyte. Each polymer is composed of a sequence of base-complementary recognition moieties which can bind specifically to corresponding contiguous bases in the analyte target sequence, and an unbranched, substantially uncharged, substantially stereoregular backbone. A reporter in the system contains (a) a polycationic tail effective to bind electrostatically to the analyte, under conditions in which the reporter does not bind to the substantially uncharged polymers, and (b) reporter groups by which the presence of the reporter can be detected.

11 Claims, 13 Drawing Sheets

OTHER PUBLICATIONS

Madeline Wu et al., "Transmission Electron Microscopic Method for Gene Mapping on Polytene Chromosomes by in situ Hybridization" Proc. Natl. Acad. Sci U.S.A. vol. 78 No. 11, pp. 7059–7063, Nov. 1981 Genetics.

Paul S. Miller et al., "Nonionic Nucleic Acid Analogues. Synthesis and Characterization of Dideoxyribonucleoside Methylphosphonates" 0006-2960/79/0418-5134$01.00/0 1979 American Chemical Society.

"33.16 Laboratory synthesis of DNA" (four pages total) by Har Gobind Khorana Professor, Massachusetts Institute of Technology.

G. Weimann, H. Schaller, and H. G. Khorana "Polynucleotides Containing Thymidine and Deoxyadenosine". (two pages total, 3836 and 3837) vol. 85, Dec. 5, 1963.

X=F, Cl, Br, I

◯-CH₂NH₂ = aminomethylpolystyrene a = succinic anhydride
b = di(succinimido)carbonate
c = 6-aminohexanol BOC=tert-butoxycarbonyl
a=di-tert-butyl carbonate
b=carbonyl diimidazole
c=dimethylamine
d=trifluoroacetic acid
e=borane-tetrahydrofuran

POLYNUCLEOTIDE ASSAY REAGENT AND METHOD

This application is a continuation-in-part of U.S. patent application for "Polynucleotide Assay Reagent and Method", Ser. No. 06/712,396, filed 15 March 1985. and U.S. patent application for "Polynucleotide Assay System and Method", Ser. No. 06/907,842, filed 15 September 1986, and Ser. No. 06/911,258, filed 24 September 1986 and incorporates by reference PCT patent application for "Polynucleotide Assay Reagent and Method" PCT/US86/00545 and "Stereoregular Polynucleotide-Binding polymers" PCT/US86/00544, both filed 14 March 1986.

FIELD OF THE INVENTION

The present invention relates to a polynucleotide diagnostic system and method.

BACKGROUND

Two general types of polynucleotide diagnostic systems, both based on hybridization between complementary segments of a polynucleotide probe and a single-strand polynucleotide analyte, have been developed. In the first type, the polynucleotide analyte is made single stranded and fixed to a solid support, such as a nitrocellulose filter. The support is then reacted, under complementary-strand annealing conditions, with a reporter-labeled probe which is complementary to a target base-sequence region of the analyte. After washing several times to remove unbound probe, the solid support is analyzed for the presence of reporter. This system has not been entirely satisfactory, particularly in clinical situations, where assay simplicity and sensitivity are required. The procedure used in fixing single-strand polynucleotide material to the solid support is somewhat involved and time consuming. The sensitivity of the system is limited because, in the usual case, each analyte molecule hybridizes with a single probe molecule and each probe generally contains no more than a few dozen reporter moieties.

A second type of polynucleotide diagnostic system involves two analyte-specific probes which are each complementary to a distinct region of the analyte polynucleotide. The first probe is linked to a solid support, and the second probe is free in solution and carries multiple reporter molecules. In practice, the analyte is mixed with the two probes under conditions which allow annealing of complementary polynucleotide strands, including annealing of both the immobilized and reporter-carrying probes to the polynucleotide analyte, to attach the reporter to the solid support by means of the analyte.

Although the dual-probe system avoids the problem of having to fix the test nucleic acid material to a solid support, nevertheless, the method has a number of limitations. First, when the test nucleic acid is derived from duplex nucleic acid, as is often the case, hybridization between the analyte polynucleotide and its complementary strand competes with the hybridization between the analyte and the two probes. Further, since the two-probe system relies on higher order kinetics than is the case for single-probe systems, it is inherently slower than a single-probe system. Also, the need for two different probes increases the cost of the system. Finally, in terms of test sensitivity, the dual-probe system suffers the same limitation as the single-probe system mentioned above—each analyte polynucleotide binds only one "reporter" probe.

SUMMARY OF THE INVENTION

It is a general object of the invention to provide, for use in detecting a polynucleotide, a diagnostic system and method that substantially overcome above-discussed problems and limitations associated with the prior art.

It is another object of the invention to provide, in such a system, a reagent having a polynucleotide-binding polymer adapted to form a base-specific duplex structure with a single-stranded polynucleotide analyte, under conditions in which complementary polynucleotide strands remain in the single-stranded state. The analyte binding can therefore be performed under conditions in which sequence-specific pairing between the reagent polymer and analyte occurs without competition from analyte-complementary strand annealing in the assay reaction mixture.

It is another object of the invention to provide in such a system, a reporter adapted to bind by electrostatic forces to the backbone of an analyte polynucleotide, under conditions in which reporter binding to the reagent polymer does not occur. The system therefore has the capacity for very high signal levels by virtue of the relatively large number of reporter molecules which can combine with each polynucleotide analyte molecule.

Providing a polynucleotide diagnostic method which is rapid, convenient, and sensitive is yet another object of the invention.

The invention includes a diagnostic reagent for use in detecting an analyte polynucleotide having a defined target base sequence. The reagent comprises a solid support, and linked to the support, multiple polynucleotide-binding polymers. Each polymer is composed of a sequence of base-complementary recognition moieties, each of which is adapted to hydrogen bond to a corresponding, contiguous base of the target region of the analyte, under selected binding conditions, and an unbranched, substantially uncharged, substantially stereoregular backbone supporting the recognition moieties at positions which allow hydrogen bonding between the recognition moieties and the corresponding contiguous bases of the target. In a preferred embodiment of the invention, the recognition moieties include purine and pyrimidine bases and the backbone is composed of a series of backbone moieties joined by achiral, predominantly uncharged linkages.

A diagnostic system for detecting a polynucleotide analyte having a defined target sequence includes the diagnostic reagent and a reporter having a polycationic tail adapted to bind by electrostatic attraction to the charged backbone of the polynucleotide analyte, but not to the substantially uncharged backbone of the reagent polymers under selected binding conditions. One or more reporter groups attached to the polycationic tail are adapted to produce a signal by which the presence of the reporter can be detected.

In the method of the invention, the polynucleotide analyte is added to the diagnostic reagent under conditions (a) in which the analyte is in a single-strand form and (b) which allow sequence-specific pairing between the analyte and the reagent polymers. After the analyte/polymer annealing reaction, the reagent is washed to remove unbound test material. The reagent and bound analyte are then reacted with the reporter, under preselected conditions in which the polycationic tail in the reporter binds electrostatically to the charged backbone of the polynucleotide but not substantially uncharged backbone of the reagent polymers. The reagent is again washed to remove unbound reporter. The presence and/or amount of analyte bound to the reagent is determined in situ by measuring the reporter signal associated with the reagent-bound analyte, or the reporter-/analyte complex is eluted from the reagent and the reporter signal in the eluate is measured, or the reporter is eluted from the reagent either with or without associated analyte, and the reporter signal in the eluate is measured.

These and other objects and features of the present invention will become more fully apparent when the following detailed description of the invention is read in conjunction with the accompanying figures.

DETAILED DESCRIPTION OF THE INVENTION

Figure 1:
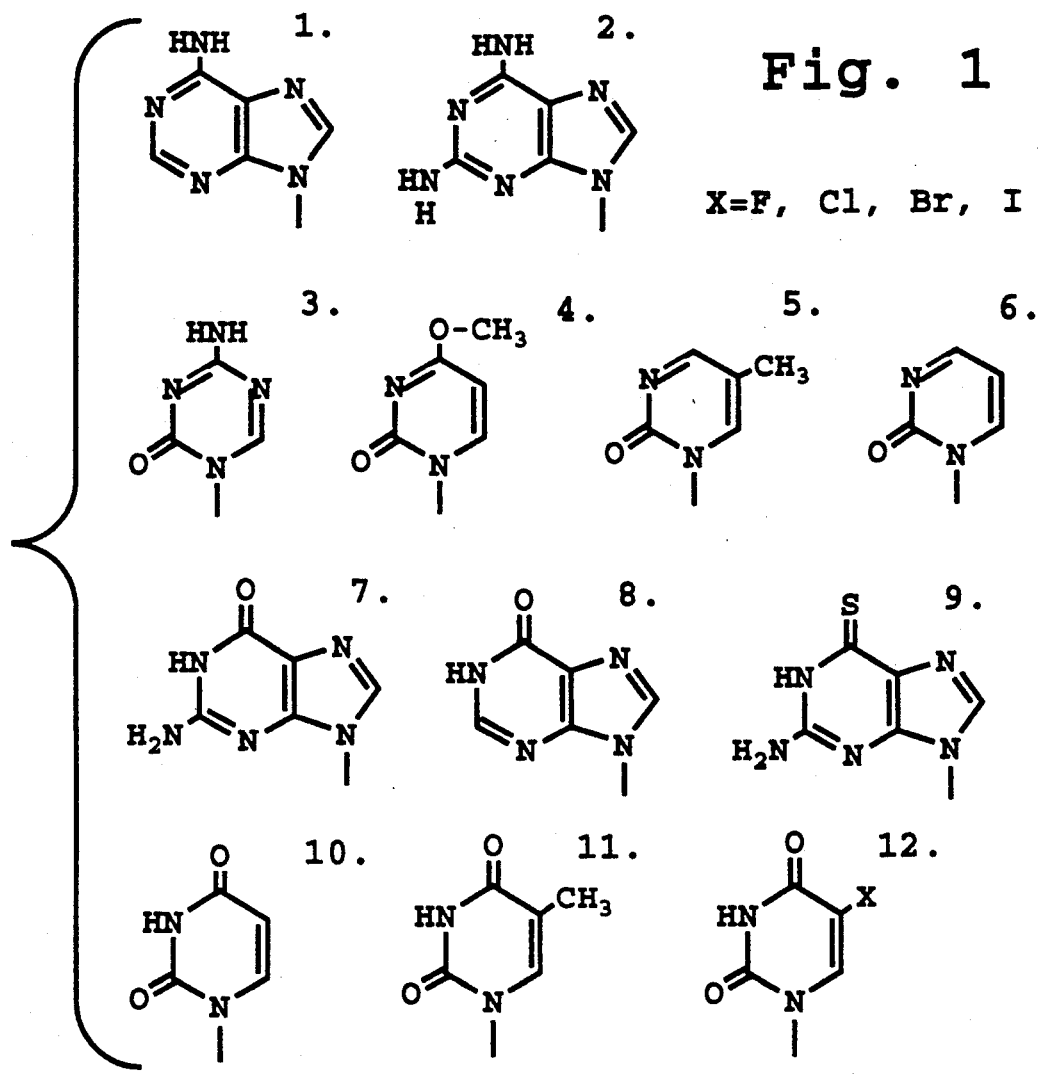
FIG. 1 shows preferred purine and pyrimidine structures used in forming polymer molecules of the invention.

The diagnostic system of the invention includes a solid support reagent composed of a solid support carrying a plurality of nucleotide-binding polymer molecules. The polymer molecules are designed to bind, with a selected binding affinity, to a polynucleotide containing a target sequence of bases. The polymer is composed of heteromeric, substantially uncharged substantially stereoregular molecules of the form:

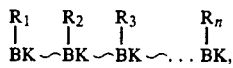

where B—$R_i$ are base-specific subunits containing a backbone moiety B and a recognition moiety $R_i$ which is selected to bind specifically by Watson/Crick base pairing to a corresponding contiguous in-sequence base in the target sequence, and the subunits are joined through their backbone moieties predominantly by achiral, uncharged linkages. The design and selection of suitable subunits for use in constructing the polymer molecules will be described in Section I below. Subunit-protective group strategies involved in subunit synthesis are discussed in Section II. Methods for synthesizing subunits are described in Section III, and methods for coupling subunits through uncharged achiral linkages are described in Section IV.

The binding affinity of the polymer molecules for the target can be selectively varied by several strategies discussed in Section V, including the choice of recognition moieties which are capable of forming either three (for greater binding affinity) or two (for lesser affinity) base-paired hydrogen bonds with the corresponding target base. The resulting polymer molecules all have substantially the same sequence of subunits and substantially the same sequence of intersubunit linkage types. In functional terms, all of the polymer molecules have substantially the same binding affinity for the target polynucleotide. Methods for assembling the polymer, once a desired subunit sequence is selected, are given in Section VI.

The polymer molecules are useful in a novel solid phase diagnostic system which is described in Sections VII and VIII. This system is based on the binding of analyte polynucleotide molecules to support-bound polymer molecules and subsequent electrostatic attachment of multiple polycationic reporter molecules to the polynucleotide, to give an amplified reporter signal for each bound analyte molecule.

I. Subunit Structure

Each subunit BK—$R_i$ is composed of two covalently linked parts: a specific recognition moiety $R_i$ suitable for hydrogen bonding to a selected base in the target genetic sequence and a backbone moiety B which links to subunits in a polymer of specified subunit order, and which also serves to position and orient its attached recognition moiety for hydrogen bonding to its complementary (in the Watson-Crick sense) base in the target genetic sequence.

A. The Recognition Moiety

The design of the subunits BK—$R_i$ which are suitable for use in forming the polymer species of the invention involves a number of structural and/or stereochemical criteria which must be met both by the backbone and recognition moieties and by the linkage between the two. The design requirement of the recognition moiety will be considered first.

The recognition moiety of each subunit must provide two or three hydrogen-bonding groups held in an unambiguous configuration adapted for hydrogen bonding to two or three of the Watson/Crick hydrogen bonding sites on a specified base at a specified position in the target genetic sequence. To avoid undesired mispairing between recognition moiety and its corresponding target base, under the conditions of use, (1) the tautomeric state of the recognition moiety should be relatively fixed, and (2) the recognition moiety should have a structure which provides a relatively rigid arrangement of the hydrogen- bonding groups. Such rigidity is best afforded by a ring structure having the polar hydrogen-bonding groups either forming part of the ring or directly attached to the ring.

The preferred recognition moiety structures include purine and pyrimidine structures which are designed to form Watson/Crick base pairing, through either two or three hydrogen bonds, with selected polynucleotide bases. The group of subunits used in polymer synthesis includes at least two recognition moieties which are base-specific for different polynucleotide bases, and preferably one or more recognition moieties for each of the four bases in a natural DNA or RNA polynucleotide. Also, as will be seen below, it is desirable to provide one group of recognition moieties, $R_i$, which are capable of base-pairing with nucleotide bases through two hydrogen bonds, and a second group, $R_j$ which are capable of binding with the same bases through three hydrogen bonds. FIG. 1 shows exemplary purine and pyrimidine type recognition moieties. The purine structures 1 and 2 are designed to bind to thymine or uracil bases, structures 3-6, to guanine bases; structures 7-9, to cytosine bases, and structures 10-12, to adenine bases. Structures 1, 4, 5, 6, 8, and 10-12 are $R_i$ type moieties adapted to bind to corresponding in-sequence bases through two hydrogen bonds, and the remaining structures are $R_j$ type moieties which form three hydrogen bonds on base pairing. As will be seen below, purine and pyrimidine nucleosides are useful in synthesizing a variety of other subunits which are suitable for use in polymer synthesis. These subunits, modified if necessary with amine protective groups, can be obtained from commercial sources, or prepared according to known methods, such as those described or referenced in Example 1.

B. The Backbone Moiety

The backbone moiety B of each subunit has the general form $N_1$—E, or $N_1$—$N_2$, where $N_1$ and $N_2$ are nucleophilic groups and E is an electrophilic group. Based on ease of subunit coupling and required stability of the resultant intersubunit linkage, as discussed below, the preferred nucleophilic groups are amino, hydroxyl and hydrazino; and the preferred electrophilic groups, and/or electrophilic linking agents, are derivatives of carbonic, thiocarbonic, carboxylic, and sulfonic acids.

Backbone moieties can have either a cyclic or an acyclic structure. While the total number of possible backbone moiety structures is very large, nevertheless, only a rather limited number of structures are of actual practical value due to a number of factors. The initial procedure by which promising backbone moieties were selected was as follows.

As a first condition, only those cyclic backbone moieties were considered which consisted of, or could be readily derived from, deoxyribose or ribose. This limitation is a practical one and reflects the difficulty and corresponding greater expense of de novo synthesizing ring structures having multiple chiral centers. In general prospective backbone moieties and intersubunit linkages expected to be suitable for polymers were selected on the basis of one or more of the following factors: feasibility of synthesis based on known reactions; expected ease of synthesis from available starting materials: simplicity of structure; and expected stability of the final backbone.

Initial screening of promising backbone moieties and intersubunit linkages was performed as follows. Space-filling CPK molecular models of duplex DNA and RNA were constructed according to parameters determined by x-ray diffraction of oligodeoxyribo nucleotides in the B-form and oligonucleotides in the A-form. In each of these constructed duplexes one of the two sugar-phosphate backbones was removed. Next, each prospective backbone was attached, if possible, to the sites on the bases form which the original sugar-phosphate backbone had been removed. Each resulting polynucleotide/polymer duplex was then examined for coplanarity of the Watson/Crick base-pairs, torsional and angle strain in the prospective polymer backbone, degree of distortion imposed on the nucleic acid strand, and interstrand and intrastrand nonbonded interactions. Special attention was paid to whether or not each amide-containing backbone could readily adopt a conformation wherein its amide moieties were planar. This is important because of the substantial energy cost required to force an amide into a nonplanar conformation.

These initial studies verified that the required unit backbone length (i.e., the $N_1$—E spacing in an $N_1$—E or activated $N_1$—$N_2$—E subunit) is 5-7 atoms for backbone moieties constituting or derived from deoxyribose or ribose (cyclic backbone structures), with a 6-atom length being optimal.

Subunit structure judged acceptable in the above modeling studies were then assessed for feasibility of synthesis (on the basis of key synthetic reactions reported in the literature, or reactions carried out on model compounds, and/or via actual synthesis of the subunits) and stability of the assembled polymer backbone (preliminary stability studies were generally carried out with suitably linked model compounds or subunit dimers). These types of studies were used to further restrict the number of candidate backbone structures. From this restricted candidate pool the cyclic backbone structures A-F shown in FIG. 2 were ultimately selected as preferred structures.

In this figure, subunits A-D containing $N_1$—$N_2$ type cyclic backbone moieties include: 2'-deoxyribonucleosides (structure A); 2'-deoxyribonucleosides substituted at the 5' and 3' positions with an amino group (structures B and C, respectively); and morpholino derivatives of ribonucleosides (structure D). Subunits containing $N_1$—E-type backbone moieties include N-aminomorpholino derivatives of ribonucleosides substituted at their 5' positions with carboxylic acid (structure E) or sulfonic acid (structure F).

The same molecular modeling approach applied to acyclic (unbranched chain) backbone moieties showed that unit backbone lengths ranging from 4-6 atoms are acceptable, in terms of polymer conformation in base-pair hydrogen bonding to single-stranded polynucleotide, with a 5-atom backbone length being optimal. This is in contrast to cyclic backbones, where a 6-atom unit backbone length is optimal. Further, the modeling work showed that the annular recognition moiety cannot be directly attached to the linear backbone moiety without severely inhibiting of coplanarity of the complementary bases and introducing undesirable interactions between the recognition moiety and the backbone. The minimum binding strain occurred when the recognition moiety was linked to the backbone moiety by a one-atom spacer, as in structures G and J. Two-atom, but not three-atom, spacers may be tolerated, although increased degrees of freedom between the recognition moieties and the linear backbone may lead to some mispairing with target bases with two-atom spacers, as in structures H, I, K, and L.

Figure 3:
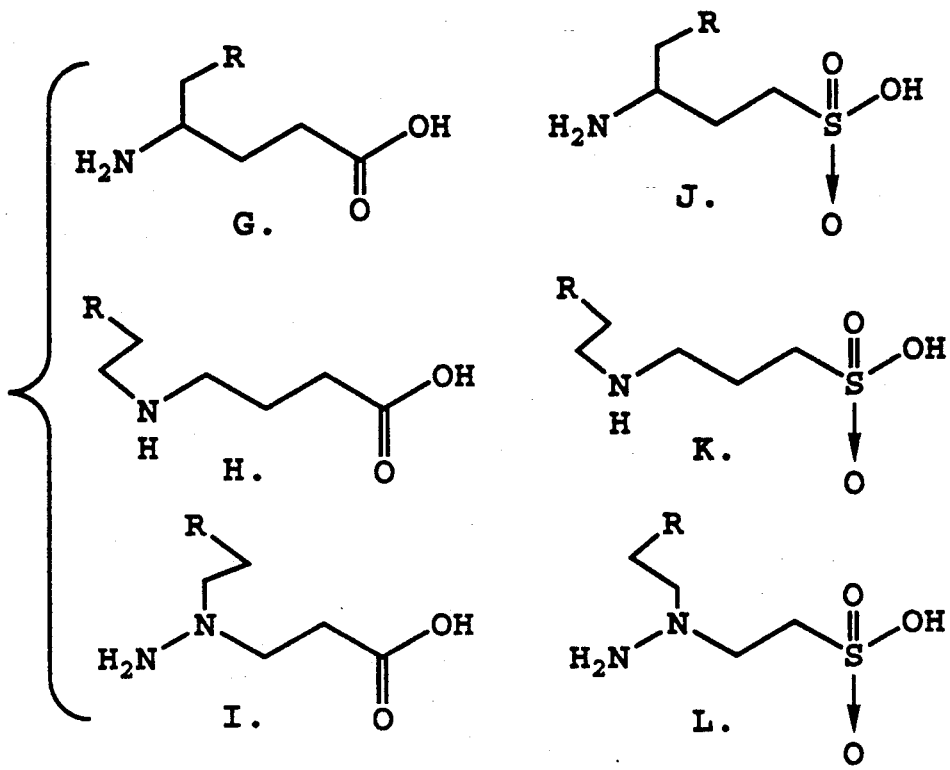
FIG. 3 shows preferred acyclic backbone moieties used in forming the polymer molecules.

The acyclic backbone moiety structures G and J shown in FIG. 3 gave a good modeling prediction for favorable base pairing to a complementary polynucleotide. Analogous structures H, I, K, and L containing a two-carbon spacer showed acceptable, but less favorable, binding conformation. The structures shown in the figure are preferred acyclic backbone moieties because of their general ease of synthesis. It should be mentioned, however, that a number of other backbone moieties are also entirely feasible and suitable—although generally not as easy and/or inexpensive to synthesize.

C. Backbone/Recognition Moiety Linkage

As indicated above, the linkage or spacer connecting the backbone and recognition moieties in the polymer subunit must meet certain design criteria which are effective to position the recognition moieties for base-pair binding to the polynucleotide bases. In the case of the cyclic backbone moieties shown in FIG. 2, modeling studies indicate that the most favorable binding conformation in the polymer occurs when the recognition moiety is attached directly to the 1' carbon of the ribose or ribose-like structures, and to the analogous 1' position of the morpholino structures. That is, the moiety is attached at normal point of attachment and with the normal stereoisomeric configuration of purine or pyrimidine bases to the ribose or deoxyribose groups of nucleosides. For the acyclic structures, one-and two-carbon atom spacers are required for placing the recognition moieties at favorable binding positions, with one-atom spacers being preferred, as discussed above.

In order to achieve a stereoregular polymer configuration required for uniform binding affinity of the polymer molecules to a polynucleotide target, it is also necessary that all of the backbone/recognition moiety linkages be either of defined chirality or achiral. The linkages are considered to be of defined chirality, for purposes of definition herein, if each of the linkages in any given subunit position in all of the polymer molecules has the same stereoisomeric configuration, or chirality. That is, although the subunits in different sequence positions may have different internal stereoisomer configurations (including achirality at specific sequence positions), substantially all of the linkages at a given sequence position among the polymer molecules have the same stereoisomeric configuration. Usually defined chirality is most easily achieved by using the same stereoisomeric configuration in all of the subunits.

Figure 2:
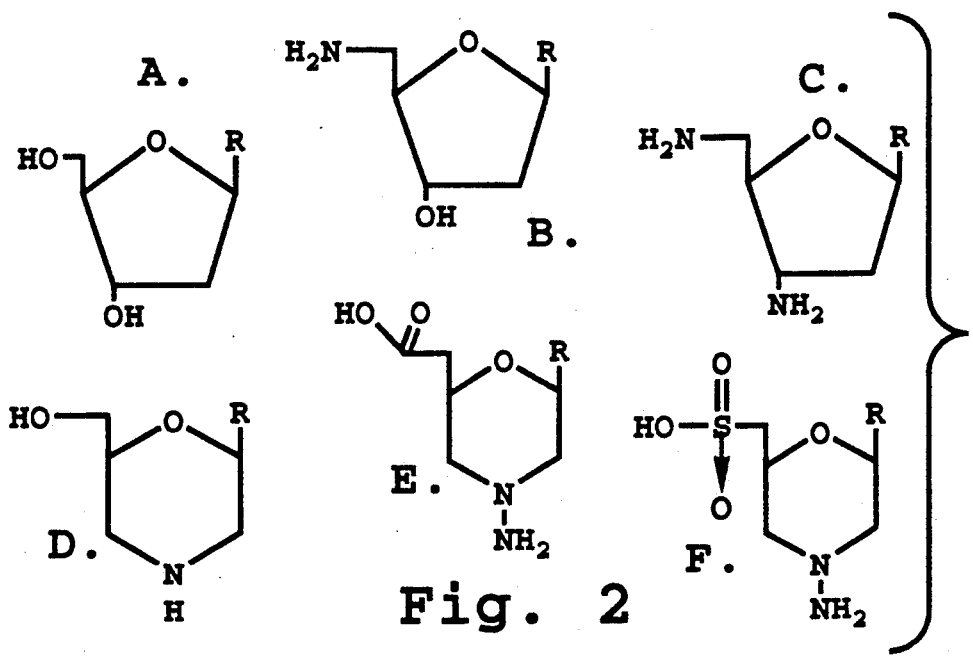
FIG. 2 shows preferred cyclic backbone moieties used in forming the polymer molecules.

For the cyclic backbone moieties, the most favorable binding occurs in nucleoside analogs having the natural D-stereoisomeric configuration shown in FIG. 2. Subunits of this type are also readily synthesized, as will be discussed below, using natural D-nucleoside starting material. With reference to FIG. 3, it is seen that only structures G and J have chiral linkages between the backbone and recognition moieties. These subunits are readily synthesized in homochiral form by using homochiral starting material as will be described. For all of the other acyclic structures shown in FIG. 3, the two-atom linkages are attached to backbone nitrogen atoms, and are therefore achiral. Also, of course, the ethylene spacers are themselves achiral.

II. Protective Group Strategies

Because of the rather high reactivity of the compounds used for activating and/or coupling the subunits, it is generally desirable, and often necessary, to protect the exocyclic ring nitrogens of the recognition moieties. Selection of these protective groups is primarily determined by the type of intersubunit linkage to be used in the polymer assembled from these subunits, and secondarily determined by the relative reactivity of the nitrogen to be protected.

Base-protected nucleosides are also useful starting reagents in a number of the subunit synthesis reactions to be described below. Methods for base protecting a number of the more common ribo- and deoxynucleosides from Example 1 are illustrated in Example 2. The methods detailed in the example are generally applicable for forming nucleosides with amine-protective groups.

When the intersubunit linkage to be used is relatively stable to nucleophiles, and particularly to ammonium hydroxide, then the standard base-protective groups used for nucleic acid chemistry are suitable. Such nucleophile-insensitive intersubunit linkages include carbamate, amide, and sulfonamide linkages. The corresponding nucleophile-sensitive protective groups for the recognition moieties include: benzoyl for the N4 of C; benzoyl or p-nitrobenzoyl for the N6 of A; acetyl, phenylbutyl, or isobutyryl for the N2 of G; and N2,N6-bisisobutyryl for 2,6-diaminopurine residues. Removal of these groups after completion of polymer assembly is effected by treatment with ammonium hydroxide.

In contrast, when the intersubunit linkage to be used is sensitive to nucleophiles, such as ammonium hydroxide, suitable protective groups are those which can be removed by strong non-nucleophilic bases—via a $\beta$ elimination mechanism. One such nucleophile sensitive intersubunit linkage is the carbonate linkage in structure A—A of FIG. 5, where Y is oxygen. Suitable protective groups for the recognition moieties removable via $\beta$ elimination include: 2-(4-nitrophenyl)ethoxy carbonyl or 2 (phenyl sulfonyl)ethoxycarbonyl for both the N4 of C and the N6 of A; and the 9-fluorenyl methoxycarbonyl for the N2 of G and the N2 and N6 of 2,6-diaminopurine residues. Removal of these groups after completion of polymer assembly is effected by treatment with the strong non-nucleophilic base 1,8-diazabicyclo[5.4.0]undec-7-ene (DBU), under stringently anhydrous conditions.

In regard to temporary protection of a nucleophile of the backbone moiety (generally N1 in the above structures). in general the polymer assembly strategy employs selected backbone-protective groups which are readily cleaved by mild acid. One primary criterion for selection of protective groups is that they be adequately stable, but not so stable that conditions required for their removal would damage the growing polymer. A principal problem in the case of polymers assembled from cyclic backbone moieties is the particular acid sensitivity of the glycosidic bond linking protected purine residues to the C1 of their backbone moieties. A secondary criterion for selection of the backbone protective group is that it be easily introduced. Based on the above, the following backbone-protecting groups are preferred: for primary hydroxyls, the di(p-methoxy)trityl group; for primary amines, p-methoxytrityl; and for a secondary amine (as in morpholino-type backbone moieties), trityl or the phenylisopropoxycarbonyl group. These protective groups can be readily removed by treatment with 0.2M dichloroacetic acid in dichloromethane.

III. Subunit Synthesis

A. Cyclic Backbone Moieties

The starting materials for subunit structures A-F of FIG. 2 include the following ribosides and deoxyribosides, which are identified according to the structure numbers of the recognition moieties given in FIG. 1: adenosine and deoxyadenosine (structure 1); 2,6-diaminopurine riboside and deoxyriboside (structure 2); cytidene and deoxycytidene (structure 3); 4-methoxy-2-pyrimidinone deoxyriboside (structure 4): 2-hydroxy-5-methyl pyrimidine deoxyriboside (structure 5); 2-hydroxypyrimidine riboside (structure 6); guanosine and deoxyguanosine (structure 7); inosine and deoxyinosine (structure 8); thioguanosine and deoxythioguanosine (structure 9); urodine and deoxyuridine (structure 10); thymidine and 5-methyluridine (structure 11;) and 5-halouridines and 5-halodeoxyuridines (structure 12).

Subunits having a deoxydeoxynucleoside subunit structure (structure A in FIG. 2) can be obtained from commercial sources or prepared via literature methods, as described in Example I.

The 5'-amino-2',5'-dideoxyribonucleosides (structure B in FIG. 2) are prepared according to methods detailed in Example 3. Briefly, the selected deoxyribonucleosides, base-protected if necessary, are reacted with triphenyl phosphine, carbon tetrabromide, and lithium azide to form the corresponding 5'-azidonucleoside, which is then reduced by hydrogenation in the presence of a palladium on carbon catylyst. The nucleosides may be obtained as in Example 1. and base-protected as in Example 2. The stereochemistry of the reactant nucleosides is preserved in forming the 5' amino nucleoside analogs.

An alternative reduction method is used in reducing the azide group of 5'-azido-5-bromo uridine, as described in Example 3.2. Here noncatalytic hydrogenation is needed to prevent removal of the ring bromine atom. In forming the 5'-amine guanosine compound, the azide is placed on the 5' position by first tosylating the 5' hydroxyl group, then displacing with azide, as detailed in Example 3.2.

The 3'-amino-2',3'-dideoxyribonucleosides (structure C in FIG. 2) are prepared according to methods detailed in Example 4. Briefly, thymidine which is protected at its 5' hydroxyl is tosylated at its 3' hydroxyl, and this is followed by an intramolecular displacement involving the 2 oxy base substituent. The resulting ring is now opened by treatment with azide, yielding a 3' azido analog of the correct stereoisomeric form. This analog can be be converted to a selected-base analog by reacting the azide compound with a selected purine or pyrimidine base. The latter may be base protected, if necessary, for subsequent subunit coupling reactions, as described below. The thymidine or other azide analog is then reduced to produce the desired 3' amine nucleoside. The stereochemistry is of the thymidine starting material is preserved in the synthesis.

Synthesis of the morpholino-type subunit derivatives represented by structure D in FIG. 2 are detailed in Example 5 for a variety of different recognition moieties. Briefly, a selected nucleoside, base-protected if necessary, is dissolved in an ammonium salt, such as ammonium biborate, and then reacted with sodium periodate to form transient 2',3' dialdehydes, which then close upon an ammonium ion to form morpholino ring having 2' and 4' hydroxyls. The compound is then treated with sodium cyanoborohydride to remove the ring hydroxyls. The ring nitrogen is preferably protected as a trityl or a 2-phenylisopropylcarbamate for subsequent subunit coupling. The stereochemistry of the nucleoside starting material is retained.

B. Subunit Synthesis-Acyclic Backbones

The 5-atom chain amino acid subunit represented by Structure G in FIG. 3 is prepared according to the general procedures outlined in Examples 6-8. Briefly, an (S)-5-carboxy pyrrolidone is converted to the corresponding stereochemically pure (S)-5-tosylmethyl-2-pyrrolidone by known methods, and then reacted with a selected purine or pyrimidine, to form the corresponding (S)-5-pyrrolidinylmethylpurine or pyrimidine pyrrolidone. The displacement reaction retains the original stereospecificity, so that the subunits which are formed are homoisomeric at the site of attachment of the recognition moiety to the backbone carbon.

The purine used in subunit synthesis is preferably contains an electron-withdrawing group at the 6 position, to reduce the reactivity of the 1 and 3 ring nitrogens, i.e., to minimize pyrrolidone coupling at a ring nitrogen. The pyrrolidone-derivized purine or pyrimidine may then be converted to the amine derivative, and base protected, if necessary, prior to the ring opening step which will be described below. Example 6.1 and 6.2 detail methods for forming the cytosine pyrrolidone and its base-protected derivative. The adenosine pyrrolidone formed in Examples 6.3-6.5 employs 6-chloropurine as the starting material, and the corresponding pyrrolidone is converted to the adenosine derivative through azide formation as described. The adenosine is base-protected, as in Example 6.6, prior to ring opening. A similar approach is used to generate base protected guanine pyrrolidone, starting from 2-amino-6 chloropurine, as described in Examples 6.7-6.9. Similar methods are used in synthesizing 2,6-diaminopurine pyrrolidone, inosine pyrrolidone, and 2-hydroxypyrimidine pyrrolidone, also as detailed in Example 6.

The pyrrolidone is then treated via a series of reactions which cleave the pyrrolidone ring to form an amino acid with a t-BOC protected amine. Examples 7.1-7.4 describe the synthesis of such t-BOC amino acids having one of a number of selected recognition moieties. In a final step (Example 5), the t-BOC protective group may be removed to form the corresponding amino acid represented by structure G in FIG. 3. The amino acid may be used directly for subunit coupling, according to reactions given below, it is preferable to activate the t-BOC protected compound at its acid group for use in subunit coupling reactions via solid-phase synthesis.

IV. Backbone Coupling Reactions

The coupling reactions used in forming the polymer molecules of the invention are stepwise reactions which join one selected subunit or subunit sequence to another subunit or sequence. For purposes of the present discussion, the coupling reactions will be described generally with respect to coupling a single subunit B—$R_1$ having a selected recognition moiety $R_1$ to another single subunit B—$R_2$ having the same or a different selected recognition moiety $R_2$, to form a dimer of the form

where $R_1$ and $R_2$ have the specific sequence shown.

A. Subunit Coupling: $N_1$—$N_2$ Backbone Configurations

Figure 4A:
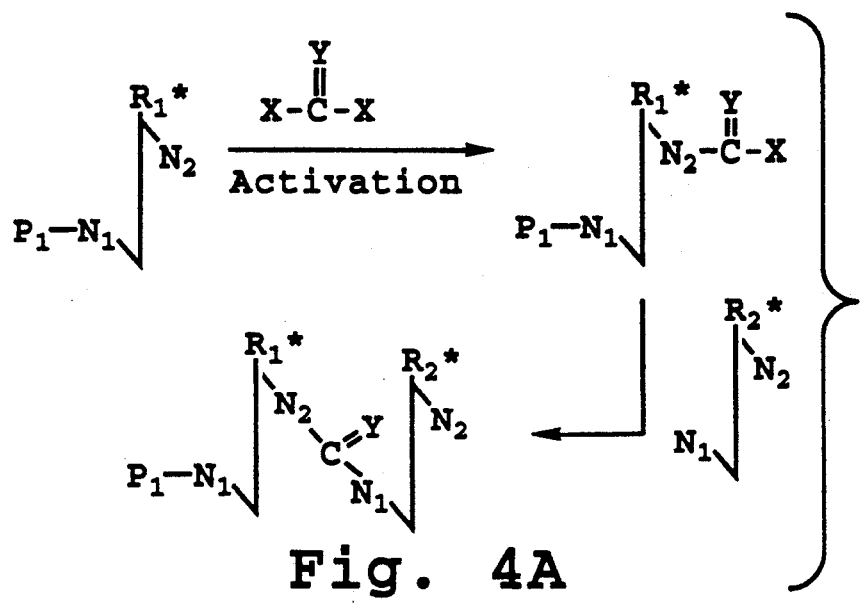
FIGS. 4A and 4B illustrate two preferred subunit assembly schemes for coupling $N_1$—$N_2$ type subunit backbones, where Y is an oxygen or sulfur and X is a good leaving group.
Figure 4B:
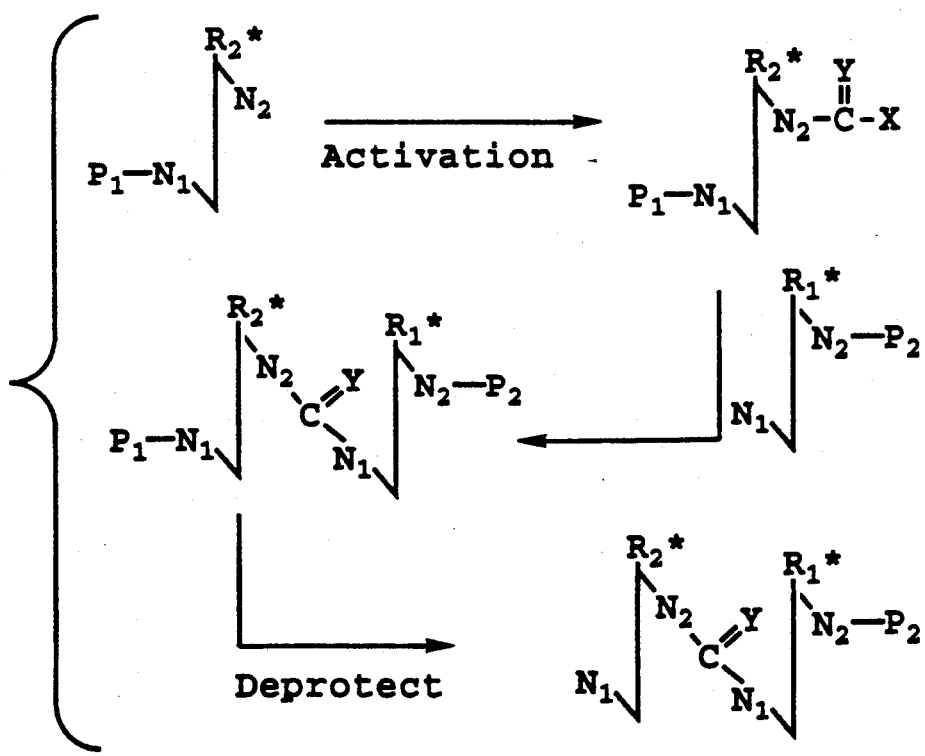

General methods for coupling subunits having an $N_1$—$N_2$ backbone configuration are illustrated in FIGS. 4A and 4B. As will be recalled from Section I above, $N_1$ and $N_2$ are nucleophilic backbone groups, such as hydroxyl and amine groups, which can be activated with an electrophile E, to form an activated $N_1$—E or $N_2$—E backbone group which can then react with a second $N_1$—$N_2$ type backbone moiety to form an $N_1$—$N_2$—E—$N_1$—$N_2$ backbone-linked dimer. The subunit backbones of this type which have been described specifically above are the cyclic backbone structures A-D in FIG. 2. In structures A and B, the activated $N_2$ nucleophile is the 3' hydroxyl group; in structure C, it is the 5' hydroxyl; and in structure D, the 6' hydroxyl corresponds to the 5' hydroxyl in structure C.

In a preferred coupling method, which is illustrated in FIG. 4A, a subunit having a selected recognition moiety $R_1$ is activated with an electrophile E. The star at the recognition moiety indicates any required base protection. As seen in the figure, the selected subunit is protected at its $N_1$ nucleophile, to ensure that (a) only the $N_2$ nucleophile is activated and (b) the activated subunit cannot self-polymerize. In structure A in FIG. 2, in which the backbone protection group is on the 5' hydroxyl, the protective group is preferably an acid-labile group, such as dimethoxytrityl (DMTO).

The activating reagent shown in FIG. 4A has the general form:

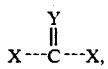

where Y is oxygen or sulfur and X is a good leaving group, such as nitrophenol or imidazole.

Activating agents, such as bis-p-nitrophenyl carbonate and carbonyldiimidazole which give the carbonyl activated subunit (X=O), are used in forming carbonate and carbamate subunit linkages. Similarly, activating agent, such thiocarbonyl-di-(1,2,4-triazole)(X=S) are used in forming thiocarbamate linkages.

Subunit activation reactions involving carbonyl activated subunits are detailed in Example 9 for the 5'-protected, 2' deoxynucleosides represented at A in FIG. 2; in Example 11 for the 5'-protected amino nucleosides represented at B in FIG. 2; and in Example 13 for the N-protected morpholino-type subunits shown at D in FIG. 2. The general reaction conditions used to activate the hydroxyl groups in these structures are generally applicable; subunit activation reactions involving thiocarbonyl-activated subunits are detailed in Example 12 for the 5'-amino nucleosides represented at B; and in Example 13, for the morpholino-type subunits shown at D in FIG. 2.

Following the activation reaction, the activated complex is purified by conventional methods, such as silica gel chromatography, and then reacted with a second subunit whose selected recognition moiety $R_2$ will form the next recognition moiety in the completed polymer. The coupling reaction is preferably carried out under mild conditions in which the activated group can react with backbone $N_1$ amine groups, but not $N_2$ hydroxyl groups. Therefore, the method is suitable for coupling subunits of the type represented by structures B-D in FIG. 2, but not subunit structure A. An advantage of this coupling method is that the second subunit—which contains an amine $N_1$ nucleophile and a hydroxyl $N_2$ nucleophile—will be coupled to the first activated subunit only through the $N_1$ amine, so it is not necessary to protect the $N_2$ backbone group. The resulting dimer subunits are therefore coupled through an $N_2$—E—$N_1$ bond, as indicated in the figure.

The oligomer can be extended by repeating the above steps of (a) activating the free $N_2$ nucleophile in the second subunit, separating the activated species from the activating agent, and coupling the activated compound with the next-in-sequence subunit, whose backbone is unprotected. This method is used particularly in forming short oligomer blocks by solution methods which will be described below and which are suitable for solid-phase block assembly.

For forming a polymer by solid-phase sequential subunit addition, the second coupling method outlined in FIG. 4B is much preferred. The second method differs from the first method in that polymer growth occurs by addition of an excess of activated subunit to an existing subunit or polymer chain, rather than, as in the first method, by addition of an unactivated subunit to an activated chain. In FIG. 4B, the existing subunit or subunit chain is shown by a subunit whose recognition moiety is $R_1$ (second line in FIG. 4B). This subunit has a free $N_1$ backbone nucleophile and an $N_2$ nucleophile which is protected by a preferably acid-stable linkage to a solid support or by virtue of being linked to a chain of subunits which are linked to a solid support. Methods of forming cyclic backbone subunits which are $N_2$ protected in this manner are described generally in Examples 19-21. The first subunit (the most recently added subunit in a growing polymer) is now reacted with an activated subunit which thereby becomes the next subunit in the polymer. This activated subunit, which is activated at its $N_2$ backbone site, and protected at its $N_1$ site, preferably by an acid-labile protective group, is prepared by methods described above with reference to FIG. 4B.

As seen in FIG. 4B, the coupling reaction adds the $N_2$-activated second subunit to the $N_1$-deprotected first subunit to couple the two through an $N_2$—E—$N_1$ bond, and form a compound which is protected at both terminal backbone nucleophile sites. This compound is now treated, for example by reaction with acid, to deprotect the acid-labile $N_1$ protective group on last-added subunit, and the procedure is repeated to build up a desired sequence polymer.

It can be appreciated from the above that the $N_2$-activated subunit which will form the most recently added subunit must be protected at its $N_1$ backbone site, to allow selective activation at the $N_2$ site and to prevent self-polymerization of the activated compound. Also the $N_1$-deprotected subunit which is to couple to the activated subunit should be protected at its $N_2$ site to allow selective reaction of its $N_1$ moiety with the $N_2$-activated subunit. Therefore, since the reacting subunits are both protected at one backbone site, the method is suitable for coupling nucleosides (structure A in FIG. 2) as well as subunits whose cyclic backbones contain both amine and hydroxyl backbone nucleophiles, such as structures B-D in this figure. The reaction methods used in coupling structure A subunits through a carbonate bond are detailed in Example 10. Briefly, a subunit containing a 5' protected backbone moiety is activated at its 3' hydroxyl, and reacted with another subunit (or growing chain) which is protected at its 3' hydroxyl. The coupling reaction is carried out in the presence of a catalyst, such as N-methylimidazole or N,N-dimethylaminopyridine, which is necessary for forming the carbonate bond. For coupling subunits containing structure B-D cyclic backbones, where intersubunit carbamate or thiocarbamate bonds are formed, much milder uncatalyzed coupling conditions, such as those described with reference to the first method above, are suitable.

The advantage of this second coupling method, for forming a polymer by solid-phase subunit addition, is that a substantial molar excess of the activated subunit can be added to the growing support-bound polymer at each polymer-addition step, to achieve subunit coupling to a very high percentage of the support-bound polymers. This insures that a large percentage of the support-bound polymers will contain the complete sequence of subunits desired. By contrast in the first method, where the growing polymer is activated at its last-added subunit, the efficiency of subunit addition is limited by the efficiency of the activations steps.

Figure 5:
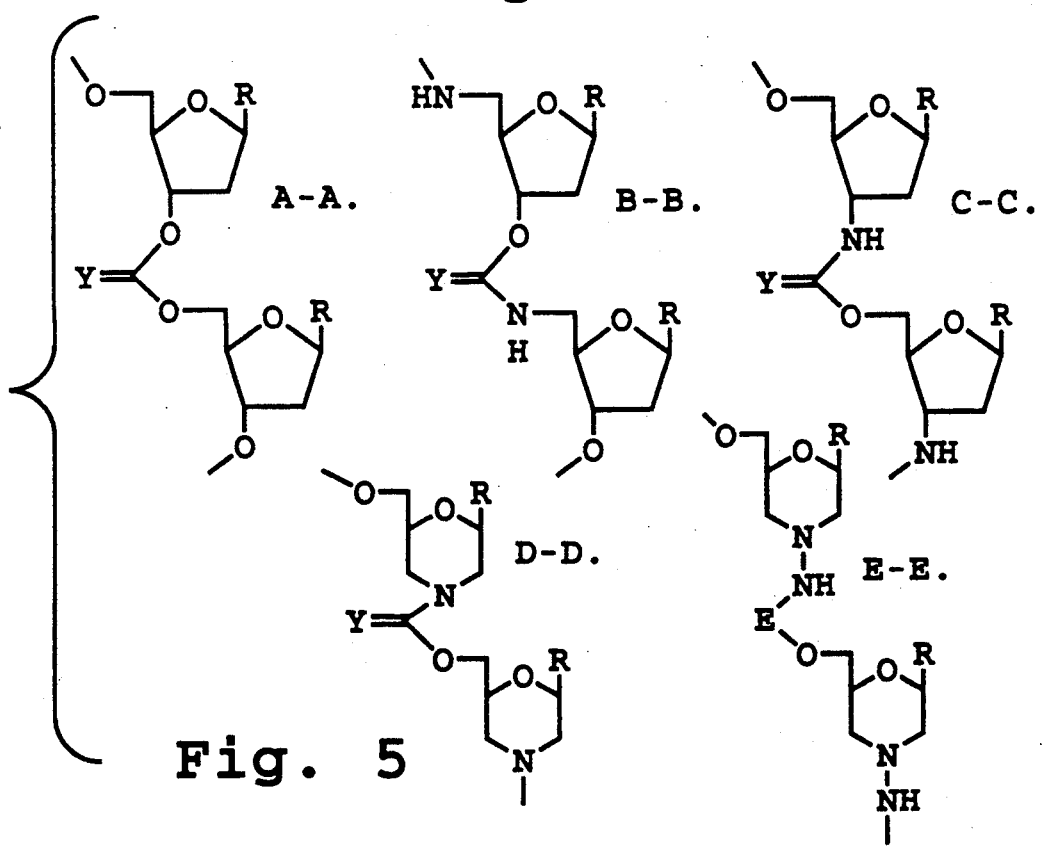
FIG. 5 shows the backbone structures of subunit dimers A—A through D—D formed in accordance with the methods illustrated in FIGS. 4A and 4B. and cyclic backbone structures formed in accordance with the methods illustrated in FIGS. 6A and 6B.

FIG. 5 shows the dimeric structures produced by coupling the cyclic backbone subunits indicated at A through D in FIG. 2. The nucleoside subunits in structure A in the figure are joined by a carbonate (Y=O). In the remaining three structures B-D, the subunits are joined by carbamate (Y=O) or thiocarbamate (Y=S) bonds. As seen from the figure, all of the subunit linkages are uncharged and achiral, i.e., do not contain chiral centers. In addition, the linkages are stable in aqueous medium, as judged by the ability of polymers to resist hydrolysis over an extended period in neutral aqueous solution.

According to another important feature of the invention, the structures, when joined to form polymers show acceptable Watson/Crick base pairing with complementary polynucleotides.

Finally, according to another important feature of the invention, polymers formed from the subunits are stereoregular. This is achieved in the structures shown by (a) using natural nucleosides or nucleoside derivatives or synthetic nucleosides having the natural stereoisomeric configuration as subunits, and (b) joining the subunits by achiral intersubunit linkages. Exemplary coupling methods are detailed in Examples 10-13.

B. Subunit Coupling: $N_1$—E Backbone Configurations

Figure 6A:
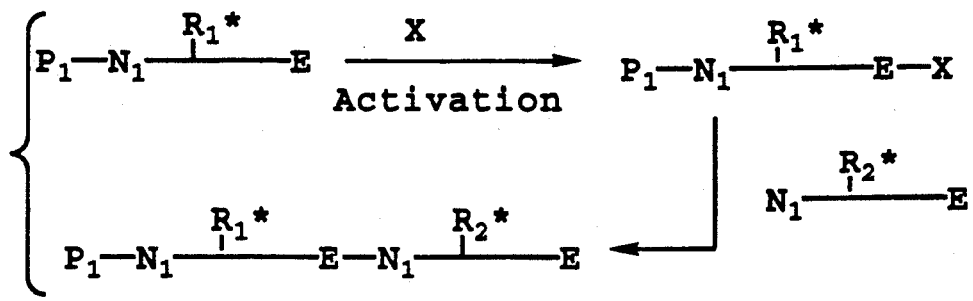
FIGS. 6A-6C illustrate three preferred subunit assembly schemes for coupling $N_1$—E type subunit backbones.
Figure 6B:
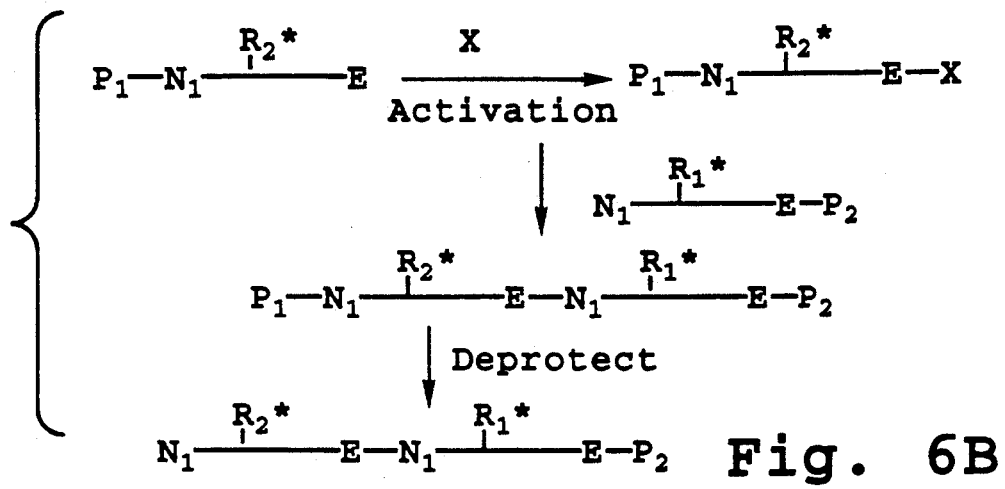
Figure 6C:
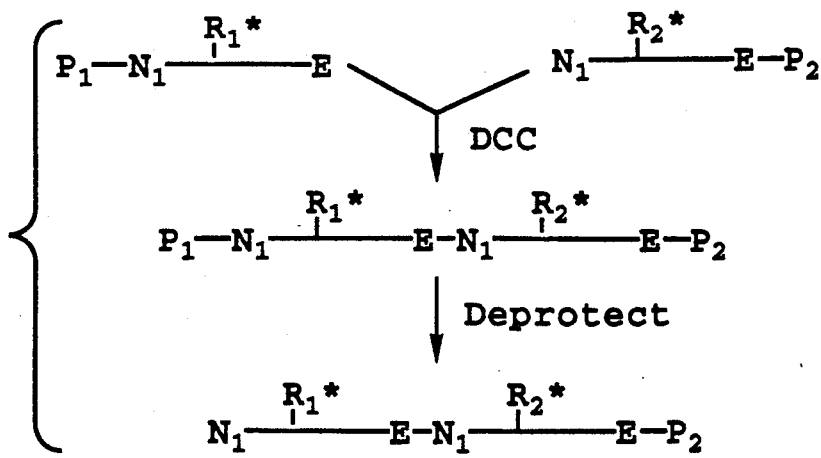

General methods for coupling subunits having an $N_1$—E backbone configuration are illustrated in FIGS. 6A, 6B, and 6C. As will be recalled from Section I above, $N_1$ is a nucleophilic backbone group, such as an amine or hydrazine group, and E is an electrophile, such as a carboxyl or sulfonyl group, which, when activated, can react with a second $N_1$—E type backbone to form an

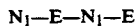

backbone-linked dimer. The subunit backbones of this type which have been described specifically above are the cyclic backbone structures E and F in FIG. 2, and the acyclic backbone structures G-L in FIG. 3. In the cyclic structures E and F, the $N_1$ nucleophile is amine attached to the 3' nitrogen on the morpholino ring. The E group in these cyclic structures is the carboxyl or corresponding sulfonyl group attached to the 6' position of the morpholino ring. In all of the structures shown in FIG. 3, the $N_1$ and E groups are respectively, the backbone amine or hydrazine and carboxylic or sulfonic acid groups on the backbone moiety ends.

The first coupling method, which is illustrated in FIG. 6A, is analogous to the method described above with reference to FIG. 4A, where a first $N_1$-protected subunit is activated, then coupled directly to a backbone-unprotected subunit which forms the next subunit in the growing polymer. The $P_1$ protective group on the subunit $N_1$ is preferably an acid-labile protective group, such as t-butoxycarbonyl or a cleavable linker bound to a solid support. Methods for protecting the $N_1$ group of cyclic backbone structures are analogous to procedures described above for protecting $N_1$ of cyclic structures A-D. Alternatively, if the polymer is to be constructed on a solid support, as described below, the backbone $N_1$ site may be protected by its attachment to a solid support, with subunit addition to the growing polymer occurring via the activated E electrophile of the last-added subunit.

The activation reaction is designed to yield an $N_1$-protected (or chain-terminal) moiety of the form P—$N_1$—E—X, where X is as described above with reference to FIG. 4, and the activated subunit has much the same reactivity toward backbone nucleophilic groups as does the activated subunit in the previously described method. That is, the activation is designed to produce much the same active coupling group as in the $N_1$—$N_2$ type backbones, but where the reactive carbonyl or sulfonyl group is provided by the backbone itself rather than by a carbonyl or sulfonyl activating reagent, as in the methods shown in FIG. 4.

The activation can be performed readily by reacting the $N_1$—E type subunit with a carbodiimide in the presence of p-nitrophenol, where the backbone electrophile is a carbonyl group, or by reacting with a carbodiimide in the presence of imidazole, 1,2,4 triazole or tetrazole, where the backbone is a sulfonyl. Subunit activation reactions involving carbonyl electrophilic groups are detailed in Examples 14 and 19. The general reaction conditions used to activate the N-amino-morpholino and linear chain backbone carbonyl groups are generally applicable to the other $N_1$—E type backbone structures shown in FIGS. 2 and 3.

Following the activation reaction, the activated complex is purified by conventional methods, such as silica chromatography, or, in the case of a support-bound activated chain, simply washed, and then reacted with a second subunit whose selected recognition moiety $R_2$ will form the next recognition moiety in the completed polymer. The coupling reaction yields a dimer whose subunits are therefore coupled through an E—$N_1$ bond, as indicated in the figure. As above, both subunits must be suitably base protected during the activation and coupling reactions.

The polymer can be extended by repeating the above steps of (a) activating the free E electrophile in the second subunit (b) separating the activated species from the activating agent, and (c) coupling the activated compound with the next-in-sequence subunit whose backbone is unprotected.

The second coupling method, which is illustrated in FIG. 6B, is directly analogous to the method described above with respect to FIG. 4B. Here a first subunit having an E-protected backbone is reacted with a second subunit with an activated E group and a protected $N_1$ nucleophile, to form a dimer linked through an $E-N_1$ bond and protected at both free backbone end groups. Where the polymer is being formed by solid-phase synthesis, the $P_2$ protective "group" takes the form of an acid-stable linkage to a solid support. The $N_1$-protected subunit is prepared and activated as above. Coupling conditions generally follow those used in the above cyclic subunit coupling reactions.

In the third coupling method, shown at FIG. 6C, the $N_1$-protected and E-unprotected subunits (or polymer units) are reacted together in the presence of a suitable E-activating agent, such as a carbodiimide, as indicated.

Figure 7:
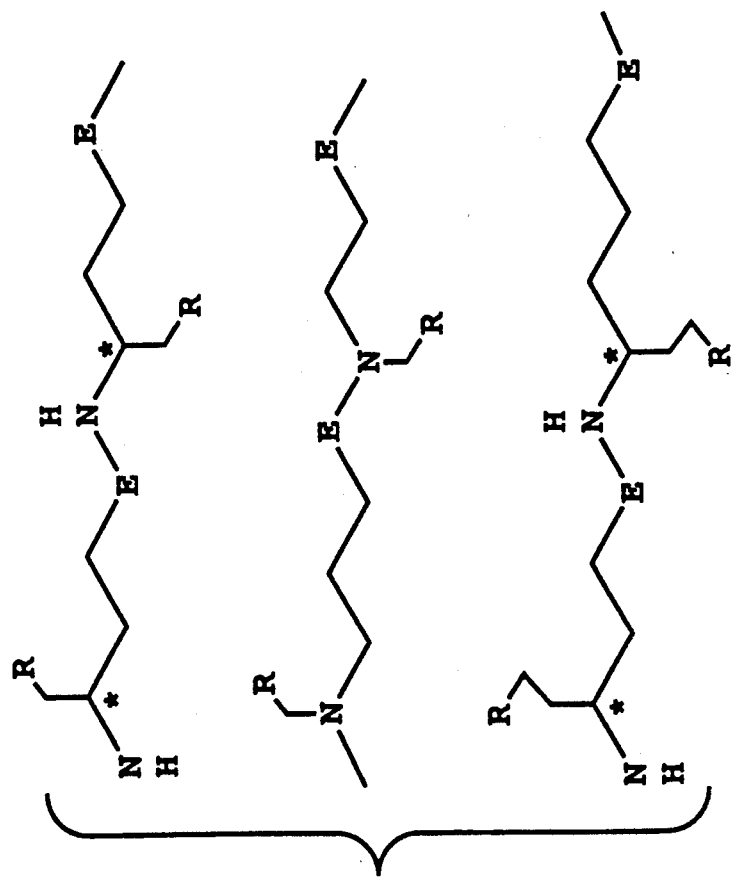
FIG. 7 shows preferred acyclic backbone structures of subunit dimers formed in accordance with the methods illustrated in FIGS. 6A-6C.

FIG. 7 shows the dimeric structures produced by coupling the cyclic and acyclic backbone subunits indicated at E-L in FIGS. 3 and 4, and at E—E through L—L, respectively, in FIGS. 5 and 7. The nucleoside subunits in structure E—E and F—F in FIG. 3 are joined through a hydrazide or sulfonyl hydrazide linkage. All of the acyclic backbone subunits, shown at G—G through L—L, are linked through amide (E=carbonyl) or sulfonamide (E=sulfonyl) bonds. As in the above-discussed cyclic backbone subunit structures, all of the intersubunit linkages are uncharged and achiral, and all of the bonds are reasonably stable in aqueous medium, as judged by the known stability of amide, hydrazide, sulfonamide, and sulfhydrazide linkages in solution.

According to another important feature of the invention, the structures, when joined to form polymers, show Watson/Crick base pairing with complementary polynucleotides.

Finally, as with the $N_1-N_2$ backbone subunits described above, all of the $N_1-E$ backbone structures shown are stereoregular. This is due to (a) the homochiral (structures E and F in FIG. 2 and G and J in FIG. 3) or achiral (structures H. I, K, and L in FIG. 3) nature of the recognition moiety attachment to the backbone moiety, and (b) the achiral intersubunit linkage.

V. Polymer Targeting Considerations

The design considerations applied in preparing a polynucleotide binding polymer for use in the invention, are governed by the nature of the target analyte and the reaction conditions under which the analyte is to be assayed. As a first consideration, there is selected a heteromeric (nonhomopolymeric) target base sequence against which the polymer is directed. This target sequence is preferably unique to the analyte being assayed, i.e., is calculated to occur only with some defined small probability (such as 1% or less) in an assay mixture containing a given number of unique-sequence bases. The probability of occurrence of a given n-base target sequence is approximately $\frac{1}{4}^n$—that is, a given n-base target sequence would be expected to occur approximately once in a polymer containing $4^n$ bases. Therefore, the probability P that a given n-base sequence will occur in polynucleotides containing a total of N unique-sequence bases is approximately $P=N/4^n$. To illustrate, the probability P that a 9-base target sequence will be found in a 20 kilobase polynucleotide is about $20\times10^3/2\times10^5$ or 0.08, the probability that a 16 base target sequence will be present is about $20\times10^3/4.3\times10^9$ or 0.0000047. From these calculations, it can be seen that a polymer having 9-16 recognition moieties specific for a defined 8-12 base target sequence should have high specificity for the target sequence in an assay mixture containing only viral genomes, whose greatest complexities correspond to about 400K of unique-sequence bases.

Similar types of calculations show that a 12 to 16 subunit polymer can provide adequate specificity for a viral or bacterial target sequence in an assay mixture containing viral and bacterial genomic material only (largest genomic sizes about 5,000 kilobases), and that a 14 to 20 subunit polymer can provide adequate specificity for a target sequence in a polynucleotide mixture containing mammalian genomic DNA material (genomic sizes of about 5 billion base pairs of unique-sequence DNA).

The polymer/analyte binding affinity, and particularly the temperature at which the polymer just binds with the target sequence (the melting temperature, or Tm) can be selectively varied according to (a) polymer length, (b) the number of hydrogen bonds that can be formed between the recognition moieties and the corresponding, contiguous bases of the analyte target sequence, and (c) backbone charge density. From a number of studies on model homopolymer duplexes, it is known that the melting temperature of oligonucleotide duplexes in the 10 to 20 bp range increases roughly 3° C. per additional base pair where the complementary bases are capable of forming two hydrogen bonds, and about 6° C. per additional base pair where the complementary bases are capable of forming three hydrogen bonds. Therefore, the length of a target sequence, which is initially selected to insure high binding specificity with the polymer, may be extended to achieve a desired melting temperature with the complementary base polymer, under selected assay conditions. Also, where the recognition moieties used in constructing the polymer are the standard nucleic acid bases, as illustrated above, the target sequence may be selected to have a high percentage of guanine plus cytosine bases for achieving a relatively high polymer/analyte melting temperature, or a relatively high percentage of adenine plus thymine bases, for achieving a relatively low melting temperature.

As will be seen below, the substantially uncharged backbone of the polymer molecules allows base-specific binding of the polymer to the analyte target sequence under a wide range of salt concentration conditions at which complementary-strand analyte reannealing does not occur, and also permits good reporter discrimination between polymer and charged analyte backbones. It will be appreciated that the polymer backbone charge can be increased up to about 1 negative charge per 4–5 subunits, to enhance solubility in water and/or ease of purification, without significantly losing these advantages of the polymer. As used herein, the term "substantially charged" is intended to include both uncharged and such slightly charged backbones.

VI. Polymer Assembly Methods

A. Geometric assembly

After selecting a desired polymer length and recognition moiety sequence, according to factors considered in Section V, the polymer is assembled, using the general subunit coupling procedures detailed above. One method of polymer assembly involves initial preparation of an appropriate set of dimers, linking selected dimers to form tetramers, linking of these to form octamers, and so on. This method is carried out in solution, substantially according to methods described with reference to FIGS. 4A and 6A above. It should be noted that all couplings need not necessarily be between oligomers of equal size. For example, often it is desirable in the last coupling to link a hexadecamer with a tetramer to give a 20-mer or to link a hexadecamer with an octomer to give a 24-mer.

A particular merit of this assembly method is that each coupling product is roughly twice the size of the precursors and so purification of the product of each coupling is simplified. Example 15 below details the the assembly of an 8-subunit carbamate-linked polymer formed by this method.(b)

B. Stepwise Assembly on a Solid Support

One preferred method for polymer synthesis is stepwise assembly on a solid support. Here the first subunit in the polymer is attached through its $N_2$ backbone group to a solid support. Typically, a solid support, such as glass beads derivatized with cleavable, preferably acid-stable, long-chain linkers are employed as the support material, and prepared for attachment of $N_2$ nucleophile, such as a 5' hydroxyl of a nucleoside, as described in Example 16. The glass beads are reacted with a subunit which has a preferably acid-labile $N_1$ protected group, and an activated $N_2$ or E backbone group, as detailed in Section III above. The coupling of various types of subunits to a glass-bead support is described generally in Examples 17–19.

After coupling the second subunit (or polymer unit which may be assembled in solution) to the support, any unreacted linker nucleophiles are capped by addition of a suitable capping reagent, such as P-nitrophenyl acetate, and thereafter the support is washed and filtered. The protecting group on the $N_1$ terminal subunit is removed, typically by acid treatment, and after neutralization, the support is then reacted with an excess of the next subunit (or polymer unit) which is activated at its free $N_2$ backbone moiety. The excess of activated subunit maximizes the number of support-bound subunits which are chain-elongated. That is, one feature of the solid support assembly method is the need for high coupling efficiencies at each subunit addition step, and the concentration of added activated subunit is selected to maximize this efficiency. Chain elongation is continued in this manner, with capping of failure sequence, after each subunit addition, until the polymer of the desired length and sequence is achieved. The general method is illustrated in Example 17 for the preparation of a 14-subunit carbonate-linked polymer, in Example 18, for the synthesis of a 19-subunit carbamate-linked polymer, and in Example 19, for the assembly of a 19-subunit amide-linked polymer.

After addition of the last-in-sequence subunit, the polymer is cleaved from the support, e.g., by treatment with a nucleophile, such as ammonium hydroxide, and the polymer is purified, such as by reverse-phase chromatography. After final removal of the terminal protective group, the assembled, purified polymer molecules are attached to a solid support, by methods to be considered below.

The polymer design principles discussed above are illustrated in Examples 15 for a solution synthesis from preassembled dimeric units and in Examples 17–19 for the preparation of a variety of uncharged achiral intersubunit linkages.

VII. Diagnostic Reagent

A. Solid Support Reagent

The reagent of the invention is formed by coupling multiple binding polymers from above to a solid support. Alternatively the polymers may be synthesized in a stepwise or block fashion, on the support, as described above for the carbamate linked polymers. The polymers may be coupled directly to (or formed directly on) the support, e.g., through an OH end group on the polymer to an OH-reactive group on a solid support such as activated agarose, cellulose, or the like. However, direct coupling often places the support-proximal subunits too close to the support to allow base-complementary binding between the analyte and the proximal subunit recognition moieties. Therefore, the polymer molecules preferably are each linked to the solid support through a spacer arm adapted to distance the polymer from the surface region of the support so as to allow substantially unhindered binding between the polymer and analyte target sequence.

Figure 8A:
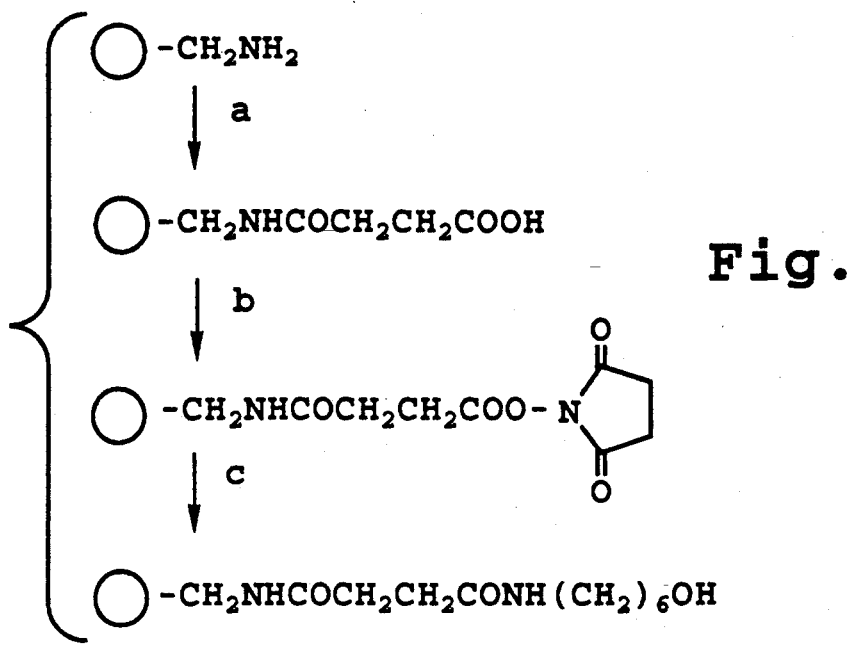
FIGS. 8A and 8B illustrate reactions for attaching spacer-arm molecules to a solid support.
Figure 8B:
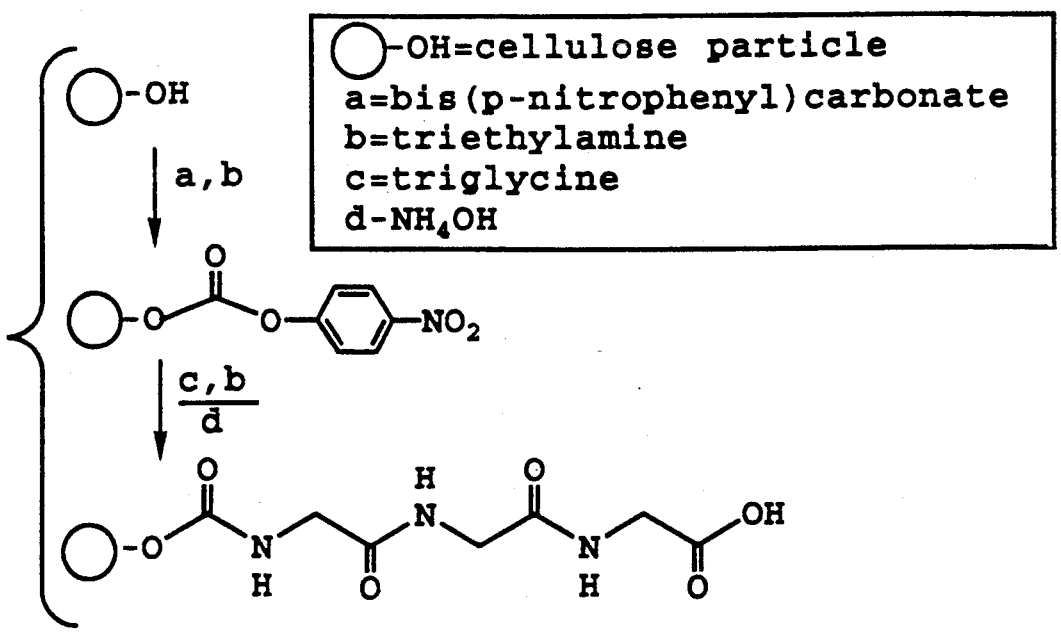

The spacer arm is preferably an unbranched chain having a total chain length of at least 6 atoms, and has suitable reactive end groups for attachment to the support, at one end, and to the polymer at the other end. A variety of types of spacer arms, particularly carbon-containing chains of various lengths and hydrophilicity, are well known, as are reactive groups used in spacer-arm coupling reactions. Example 20 below describes the synthesis of an aminohexyl spacer arm, its attachment to the 5' end of a carbamate-linked polymer, and coupling to a solid support. Example 21 below details the preparation of a polymer support having multiple surface-bound, linear-chain spacer arms, for use in forming a diagnostic reagent having carbamate-linked polymers. The method of Example 21 is illustrated in FIG. 8A. The support shown in the figure is an aminomethylated polystyrene which is first reacted with succinic anhydride to form a carboxylated derivative. Activation of the support with di(succinimido)carbonate and reaction with 6-aminohexanol leads to the 13-atom terminal-hydroxyl spacer arm shown. FIG. 8B also shows another method of preparing a cellulose support with spacer arms which is preferred because of its simplicity and reduced cost.

Preferred solid supports include agarose, cellulose, nitrocellulose, latex, polystyrene, and other commercially available strip or particle-bead support material having surface-reactive or activatable groups which allow efficient coupling of polymer molecules, particularly through polymer-bound spacer arms. The concentration of polymers coupled to the support surface is preferably selected so as to allow a 10–1000 fold molar excess of polymer molecules to analyte molecules when a suitable sample volume of assay material is mixed with the support, in the diagnostic procedure, as will be described below. A procedure for coupling a target binding polymer to agarose beads through the aminohexyl spacer arm and to cellulose particles through a triglycine spacer arm is described in the same example.

B. Reporter

The reporter of the diagnostic system of the invention is composed of two parts: (1) a polycationic moiety or tail designed to bind electrostatically to a fully charged polynucleotide, under conditions where the reporter does not bind to the substantially uncharged binding polymer carried on the diagnostic reagent, and (2) one or more reporter groups attached to the tail adapted to produce a signal by which the presence of the reporter can be detected. Polycationic, as the term is used herein, encompasses tails having two or more suitably spaced cationic groups.

The polycationic moiety of the reporter is constructed to provide two or more moieties having a positive charge at a selected pH, preferably in the pH range of 3.0 to 8.0. The number of cationic moieties in the reporter tail may vary from two up to about 8 or more, according to the total electrostatic attraction required to bind the reporter to the polynucleotide analyte. For reporters having relatively large reporter groups, such as enzymes, multiple electrostatic bonds may be required to attach the reporter tail to the analyte backbone.

The cationic groups are spaced appropriately for ionic binding to a corresponding number of anionic sites along the backbone of a polynucleotide analyte. Because of the considerable flexibility of single strand nucleic acids, this spacing between cationic sites can range from a minimum of 2 atoms, e.g.,

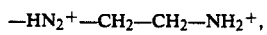

to a practical upper limit of about 8 atoms. The spacing between cationic moieties need not be uniform, as in the case of a backbone prepared from spermine which contains both 3- and 4-atom spacings, and the cationic moieties can be either directly in the chain, as in the case of a spermine-derived backbone, or pendent from the chain, as in a poly(glycine-ornithine) or poly(glycine-arginine) backbone prepared by standard peptide synthesizing methods. Further, the cationic moieties can constitute primary, secondary, tertiary, or quaternary amines, or a combination thereof. The cationic moieties may also consist of hydrazino or guanidino groups, or weakly basic groups such as imidazole, or combinations thereof, in which case reporter labeling of the analyte must be carried out at a pH sufficiently low to protonate these weakly basic groups. The backbones are preferably linear, but may also be branched, such as in polyethyleneimine.

Methods for constructing cationic tails having primary and secondary amine moieties are described in Example 29.2. Preparation of cationic tails having tertiary amine moieties are described in Example 27, and preparation of tails having quaternary amine moieties, in Example 28. Further, reporter tails containing only primary amine moieties (such as oligomers of glycine-lycine) or containing guanidine moieties (such as oligomers of glycine-arginine) or containing weakly basic groups (such as oligomers of glycine-histidine) are readily prepared by well-established methods of peptide synthesis.

Figure 9:
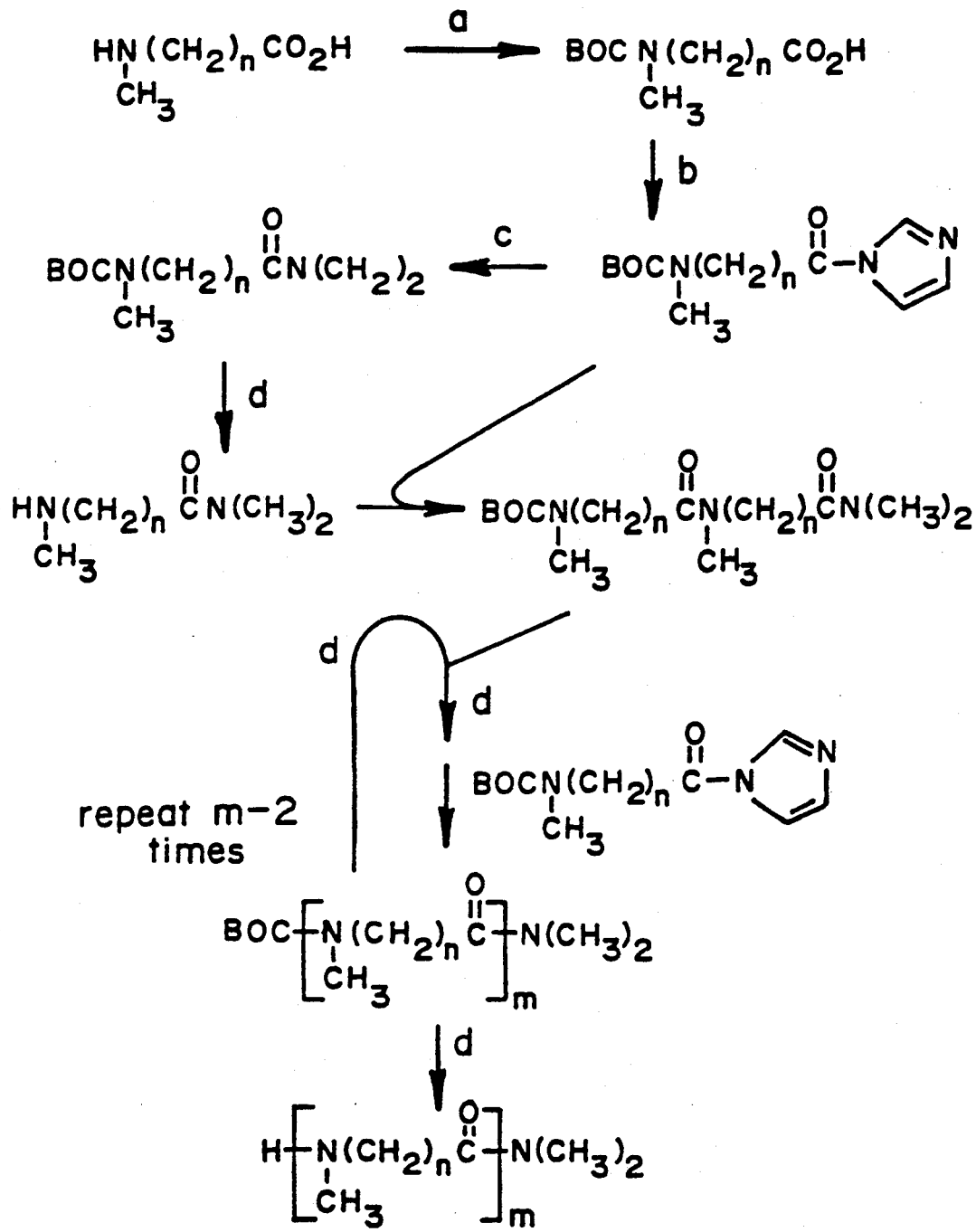
FIG. 9 shows a general method for synthesis of polyamides from N-methyl amino acids.
Figure 10:
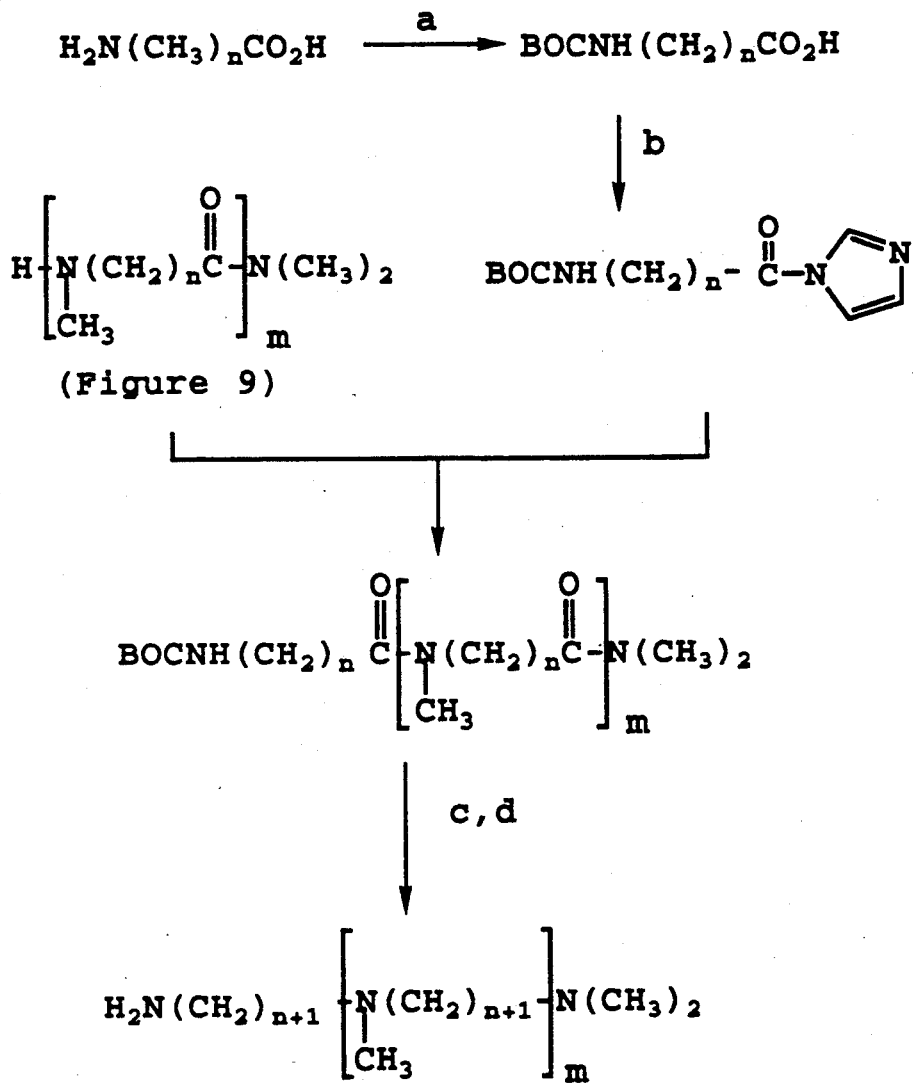
FIG. 10 shows a method for synthesis of polyamines having a terminal primary amino group.
Figure 11:
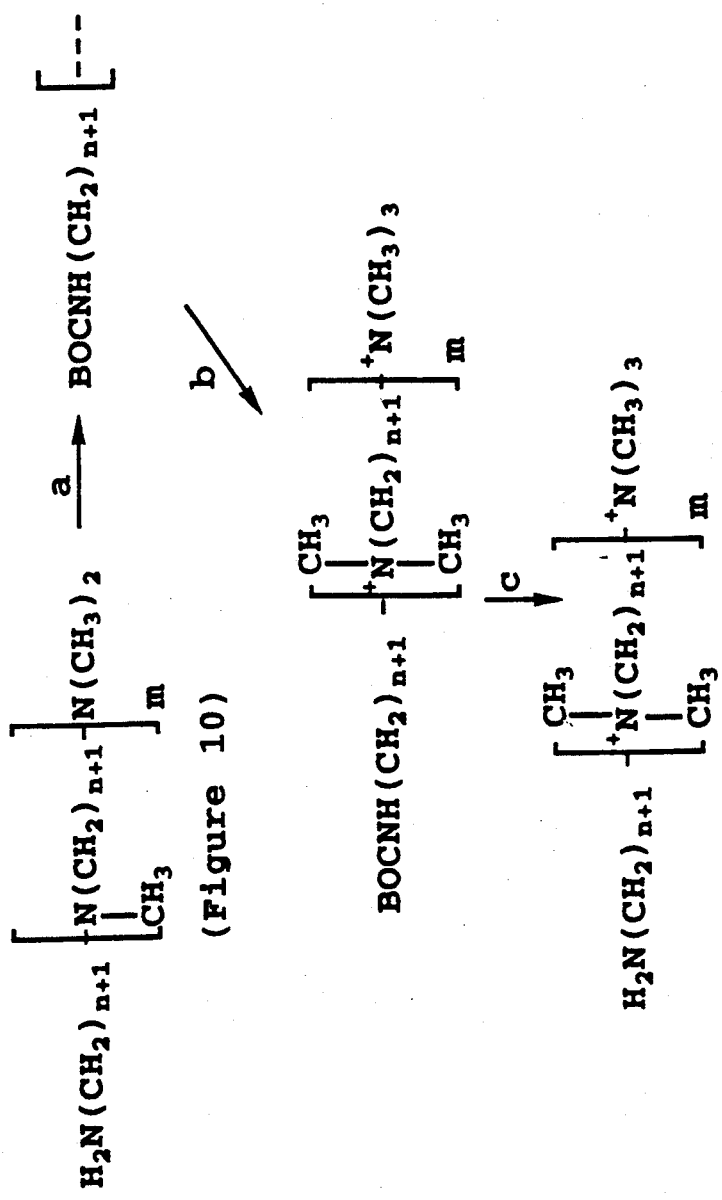
FIG. 11 shows the preparation of the quaternary ammonium cationic tail having a terminal primary amino group.

In addition, general methods for constructing a cationic tail suitable for use in the invention are outlined in FIGS. 9-11. With reference first to FIG. 9, an N-methyl amino acid is N-protected with di-t-butyl dicarbonate (BOC), activated with carbonyl diimidazole, then coupled through an amide linkage to dimethylamine. After deprotection, the amide is reacted with an N-protected, carbonyl diiamidazole-activated amino acid from above, to form a diamide compound which is shown at the center in FIG. 9. The deprotection reaction and reaction with N-protected diimidazole-activated amino acid, are repeated until the desired-length polyamide is formed. Details of the synthetic reactions are set forth in Examples 23-25.

A reporter group is most readily attached, typically, to a primary amine group in the polycation. To attach a primary amine to the secondary-amine end of the FIG. 9 compound, according to one suitable method, an amino acid. e.g., 4-amino butyric acid, is BOC-protected, activated with diimidazole, and reacted with the deprotected polyamine, as illustrated in FIG. 10. The resulting BOC-protected compound can then be reduced, after treatment with trifluoroacetic acid to remove the BOC group, by reaction with borane-tetrahydrofuran. These procedures are described in Examples 26-27.

FIG. 11 shows a reaction scheme for converting polyamine, such as synthesized above, to a polyquaternary ammonium salt. The procedure involves protection of the terminal 1° amine followed by reaction with methyl iodide, to form the poly quaternary ammonium salt, and deprotection with trifluoroacetic acid. Example 28 below gives details of the method.

The one or more reporter groups in the reporter should be (1) readily attached to the cationic tail, and (2) capable of generating an easily detected signal, either when the reporter is bound to a polynucleotide backbone, or after the reporter has been eluted from the analyte. Small reporter groups that include chromophores, such as nitroaniline or other strongly absorbing dyes, and fluorophores, such as dansyl or rhodamine-based fluorescent molecules, are suitable and have the advantage that they can be readily detected by photometric equipment, or in the case of dyes, by visual inspection. Radioisotopic reporter groups may provide advantages in diagnostic sensitivity, but reporter detection may be more complex and expensive. Stable paramagnetic molecules, such as nitroxide spin labels, may also be used, the binding of the reporter to the polynucleotide being detected by broadening of electronic spin resonance (esr) absorption lines characteristic of immobilized paramagnetic species.

Another class of suitable reporter groups include ligand molecules, and preferably small antigenic molecules capable of binding specifically and with high affinity to anti-ligand molecules. Exemplary ligand/antiligand pairs include antigen/antibody, lectin/carbohydrate, and biotin/avidin. The anti-ligand molecule is part of a signal producing binding conjugate which also includes a signal producing group, such as a chromophore, fluorophore, or enzyme by which the presence of ligand groups can be detected, when ligand/antiligand binding has occurred.

The reporter may have enzyme reporter moieties, particularly, as noted above, where the reporter tail has more than two cationic groups. Representative classes of enzymes are oxidoreductases, typified by luciferase; glucose oxidase; galactose oxidase and catalase; hydrolases, typified by various kinds of phosphatases; glycosyl hydrolases, such as $\beta$-galactosidase; peptidases; and lyases.

It should be mentioned that for large reporter moieties, such as enzymes, the reporter may actually comprise a single reporter moiety with multiple polycationic tails linked thereto. These multi-tailed reporters are readily prepared, as illustrated in Example 30.

Figure 12:
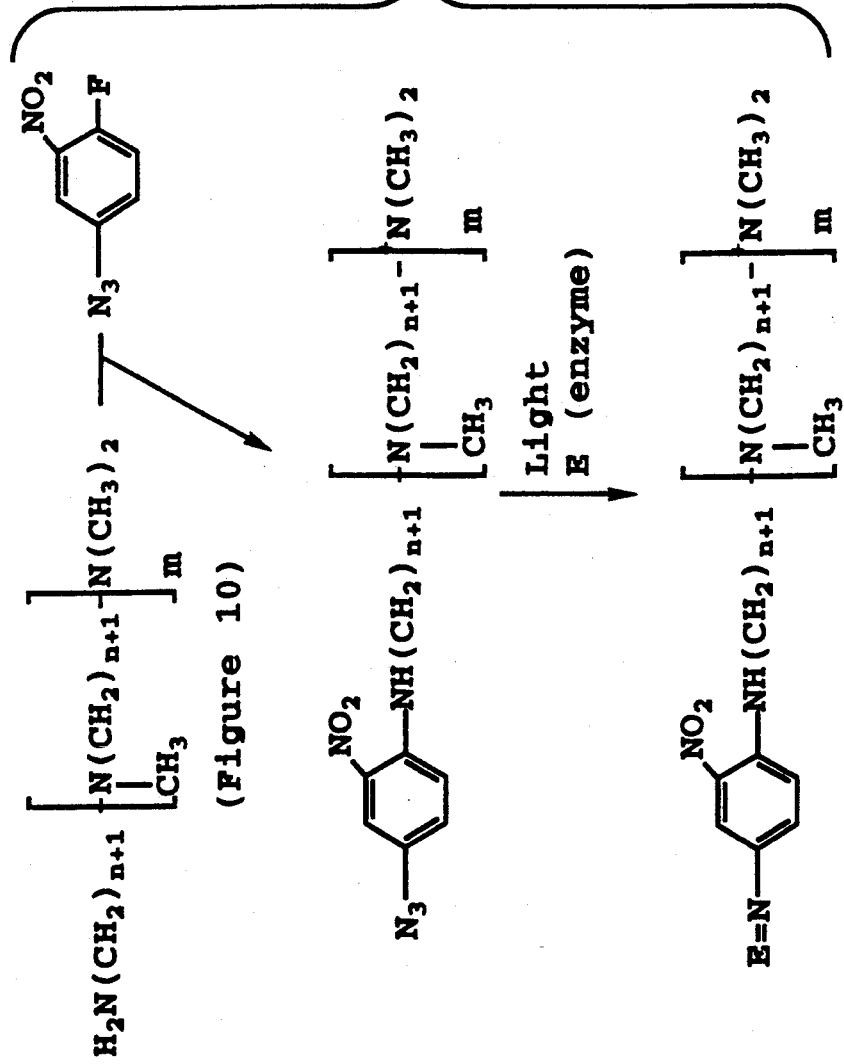
FIG. 12 illustrates a reaction for preparing a multi-charge enzymatic reporter according to an embodiment of the invention.
Figure 13A:
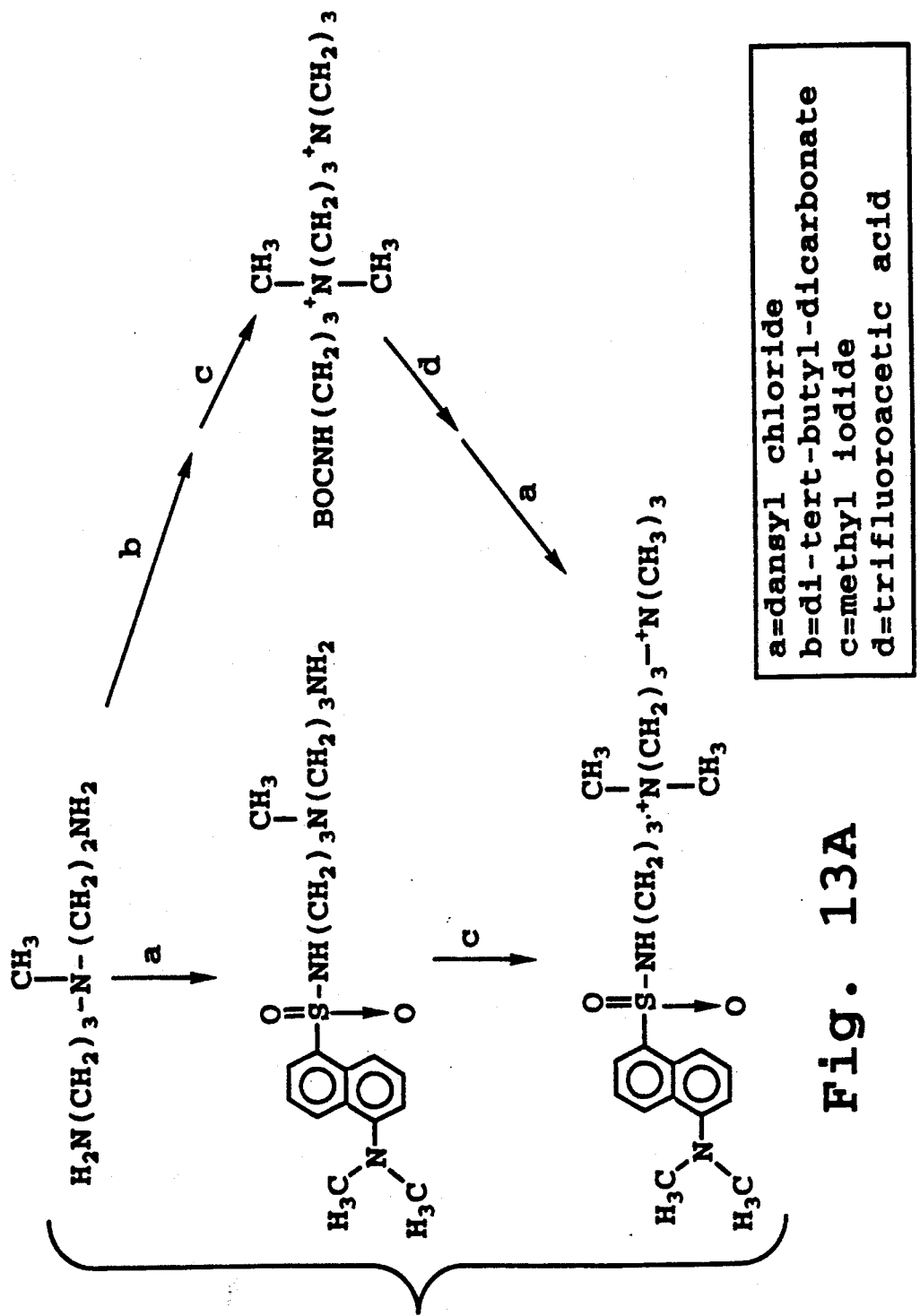
FIGS. 13A and 13B illustrate reactions for preparing two-charge and three-charge fluorescent reporters according to an embodiment of the invention.
Figure 13B:
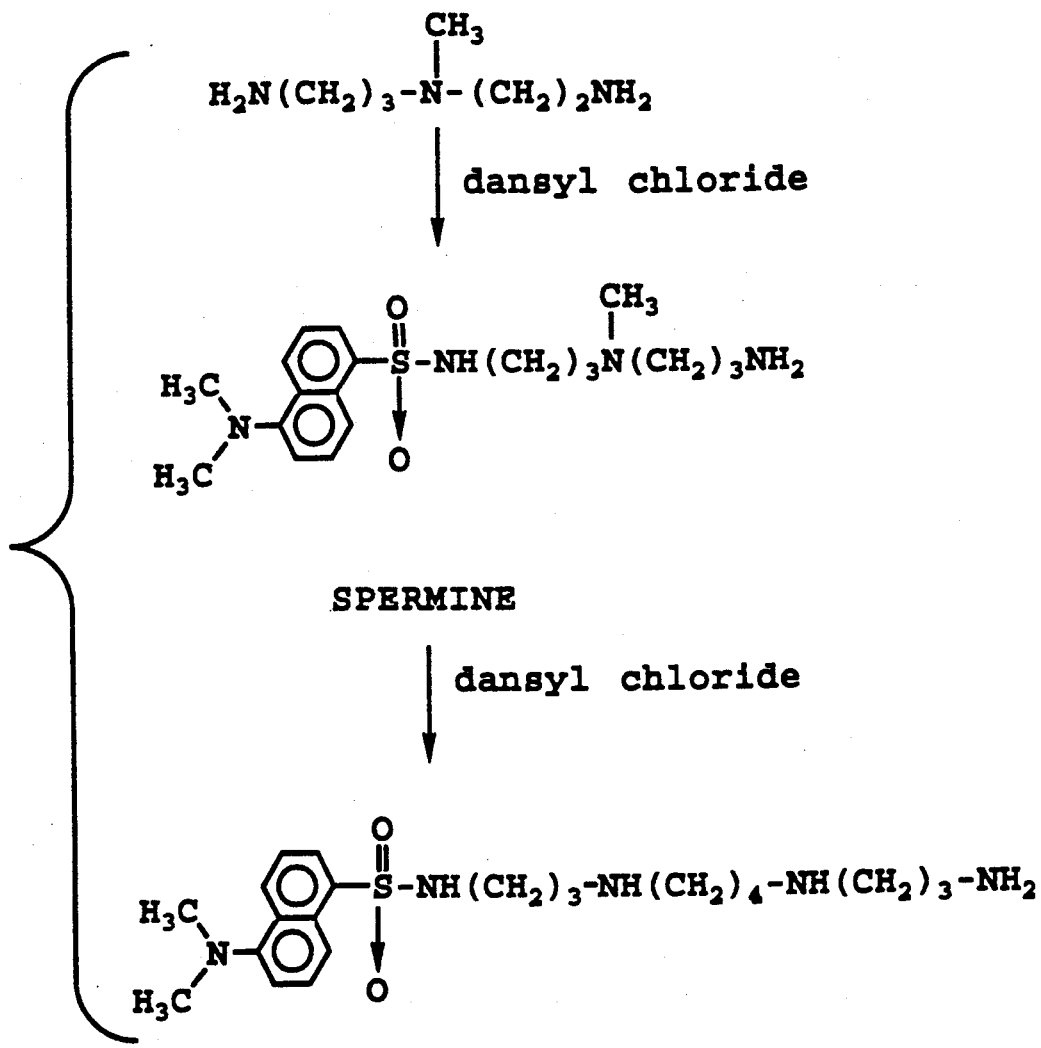

Typically the reporter group or groups are coupled to an amine of the polycationic tail, and preferably a primary amine, according to known coupling methods. In one preferred method, illustrated in FIG. 12, a polyamine is reacted with a suitable bifunctional coupling agent, such as 4-fluoro-3-nitrophenylazide, and then coupled to a reporter group, such as an enzyme. A variety of bifunctional reagents for coupling amines to reactive reporter groups such as amine, carboxyl, OH, and sulhydral groups, are well known. A detailed method for forming a tetracationic reporter with an alkaline phosphatase reporter group is given in Example 30. In another preferred procedure, illustrated in FIG. 13, reporters are prepared by reacting bis-3,3'-aminopropylmethylamine or spermine with an amine-reactive dansyl group. The reaction scheme in the figure also indicates how the amino moieties of the reporter tail can be fully alkylated, if desired, before or following reporter coupling to the tail. Details of the procedure are given in Example 29.

VIII. Diagnostic Method

This section describes the use of the diagnostic system described above for determination of a polynucleotide analyte. The analyte may be one which normally exists in a single-stranded form, such as messenger RNA (mRNA), ribosomal RNA (rRNA) or a single-stranded RNA or DNA viral genome, or one which exists under physiological conditions in a double-stranded or duplex form, such as double-stranded viral RNA, RNA/DNA viral replicative intermediates, and duplex DNA, such as that derived from a virus, a bacterium, or eucaryotic cell. The considerations and rationale used in selecting a target sequence in the analyte polynucleotide, against which the reagent polymers are targeted, are considered in Section V.

In performing the diagnosis, a sample to be assessed for analyte is collected, typically by conventional clinical sample-handling techniques. Where the analyte is a virus or bacteria-derived polynucleotide, it is often useful to first process the sample to remove larger nonanalyte cell material. For example, in assaying for the presence of a viral pathogen, it is often useful to filter the sample through a 0.2 micron pore-sized membrane to remove bacterial material. In assaying for the presence of a bacterial pathogen, it is often useful to filter the sample through a 1.0 micron pore-sized membrane to remove eucaryotic cells, which may also be present in the sample. Typical sample preparation methods are described for diagnosis of viral pathogens in Examples 31 and 32.

To prepare the sample analyte material in a form suitable for binding to the reagent polymer, the sample should be treated to free the organism's nucleic acid. For organisms lacking cell walls, detergents and/or chaotropic salts are generally adequate. For organisms having cell walls, alkali (when the analyte is DNA) or suitable enzymes (e.g., lysozyme for many bacteria) can be used. If desired, the freed nucleic acids can be conveniently separated from proteins and other contaminants by addition of a chaotropic salt (sodium trichloroacetate) followed by selective precipitation of the nucleic acid with ethanol.

One efficient method for freeing and isolating nucleic acid material from viral or cell components has been described by the inventor in Anal Biochem (1983) 133:79. The method, which is detailed in Example 31, involves suspending the sample in 4M trichloroacetate, 100 mmol EDTA, to denature and solubilize proteinaceous material, then precipating freed nucleic acid material in the salt solution by the addition of an equal volume of cold ethanol. A carrier polynucleotide, such as polyuridylic acid, may be added to facilitate nucleic acid precipitation. After a short chilling time, the precipitated nucleic acid is pelleted by centrifugation, and washed with aqueous ethanol to remove salt.

The nucleic acid fraction is resuspended in annealing buffer having a selected salt concentration and a divalent cation chelating agent. An annealing buffer containing about 100 mmol or less of monovalent salt, such as NaCl, and about 10 mmol chelating agent, such as EDTA, is generally suitable for binding of a polynucleotide which exists normally in a duplex DNA form. Higher salt concentrations, particularly above about 0.5M. tend to allow duplex formation between complementary polynucleotide strands, leading to competition between the reagent polymer and the complementary strand for binding to the analyte polynucleotide. Duplex formation between complementary polynucleotides is also inhibited by the chelating agent, which acts to sequester $Mg^{+2}$ and $Ca^{++}$ ions in the annealing mixture. Where the analyte is an RNA, it may be advantageous to treat the sample with DNase to prevent competition between dissociated DNA and the RNA analyte for binding to the reagent polymer. Conversely, when the analyte is DNA, it may be advantageous to treat the sample with RNase.

The annealing reaction is preferably carried out at a temperature which is about 5° C. to 15° C. below the melting temperature of the analyte/polymer duplex structure which forms during the reaction period. This annealing temperature favors faithful base-sequence pairing between the analyte target sequence and the polymer. As indicated above, where the analyte polynucleotide normally exists with its complementary strand as a duplex structure, the reaction temperature is preferably higher than the melting temperature of the native polynucleotide duplex, to avoid undesired pairing of the analyte with its complementary polynucleotide competing with the desired pairing of the analyte with the reagent polymer. At an annealing buffer concentration of about 100 mmol or less in monovalent cation, annealing temperatures in the range of 24° to 60° C. are generally suitable. As noted earlier the actual optimal annealing temperature is a function of the length of the binding polymer, its ratio of A+T to C+G recognition moieties, and the concentration of modifiers such as formamide.

Depending on the structural characteristics of the polymer, as discussed above, the melting temperature of the analyte/polymer duplex structure may be substantially higher than a preferred reaction temperature, such as 37° C., in the particular annealing buffer employed, such as 100 mmol monovalent salt. In such cases, it may be convenient to lower the melting temperature of the polymer/analyte duplex structure to the desired temperature by the addition of a denaturant such as formamide. To determine the amount of formamide needed to achieve the desired melting temperature, the melting curve of the polymer and the target sequence, which may be a synthetic oligonucleotide having the analyte target sequence, is determined by conventional means, and at a number of different denaturant concentrations, and, in the case of added formamide, typically ranging between about 5% and 50% by volume of denaturant. From this determination, the amount of formamide needed in the annealing buffer in order to achieve a melting temperature about 5° to 15° above the desired reaction temperature is determined.

The analyte sample in the reaction buffer is added to the diagnostic reagent preferably under conditions where the binding polymers of the reagent are present in a 10–1000 molar excess over the molar concentration of analyte molecules in the assay mixture. The polymer/polynucleotide annealing reaction is carried out at the selected reaction temperature for a period sufficient to allow substantial polymer/analyte annealing, typically between 10 minutes and 3 hours. The solid-support reagent is washed one or more times to remove unbound material.

Reporter is then added to the washed reagent under preselected conditions to bind reporter molecules to the fully charged backbone of the reagent-bound analyte. The spatial/charge characteristics of the reporter, which permit selected binding of the reporter to the polynucleotide backbone have been discussed above.

Figure 14:
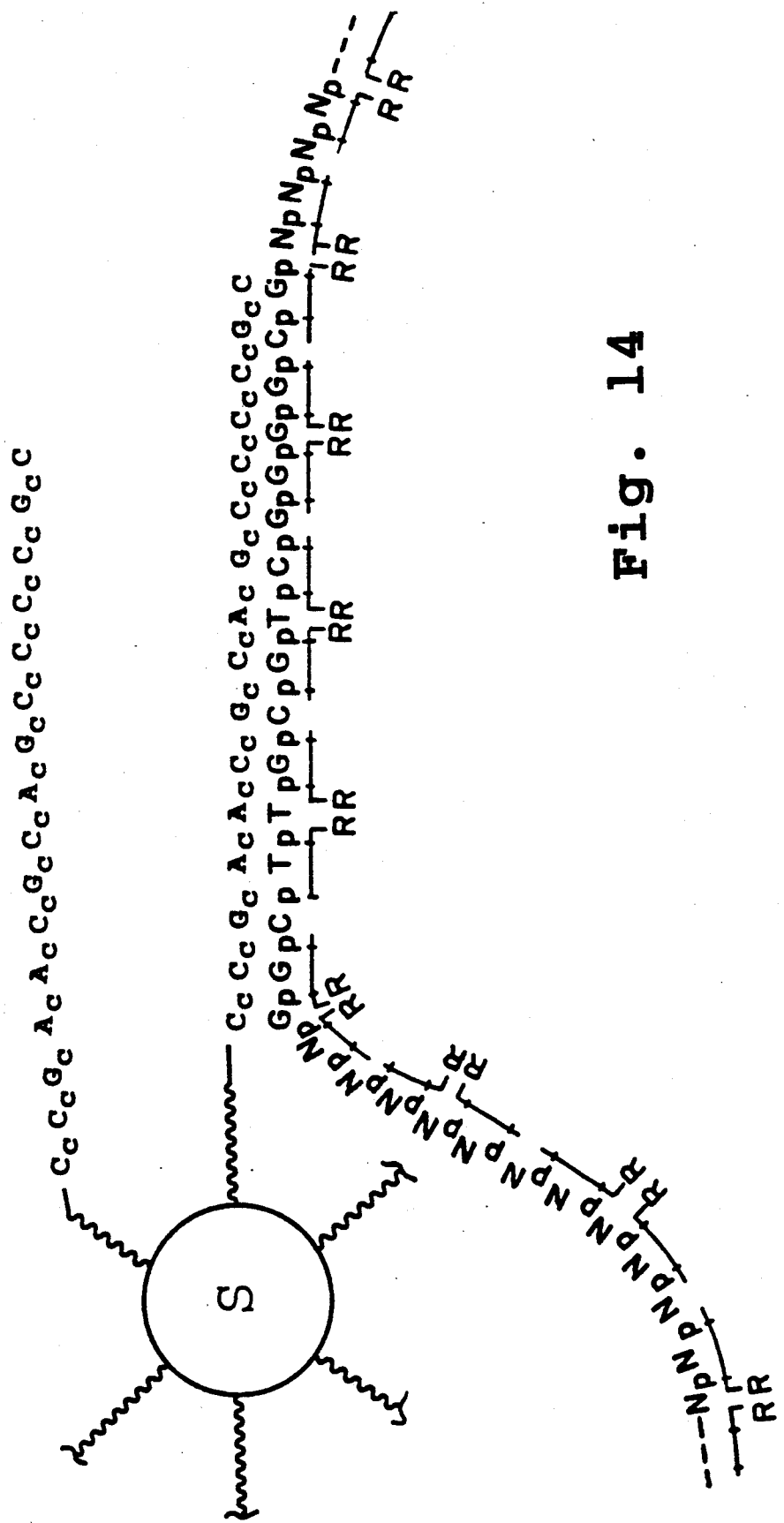
FIG. 14 illustrates various components involved in the diagnostic system and method of the invention.

The binding components in the diagnostic system, as they function in the diagnostic method of the invention, are shown below in FIG. 14. Here "S" is the solid support having a number of binding polymers attached to its surface through spacer arms indicated by sawtooth lines, and the "c"s represent carbamate intersubunit linkages. The reporter has a dicationic tail and an R reporter group. For illustrative purposes, each polymer has the sequence of recognition moieties complementary to the selected 16-base target sequence in *Herpes simplex* virus. Types I and II, as described in Example 31. The base-complementary binding of one of these polymers to the target sequence in a *Herpes simplex* analyte polynucleotide is shown.

The reporter shown in the figure is the dicationic reporter from Example 29. Each reporter is adapted to bind through electrostatic attraction to a pair of adjacent phosphodiester bonds in the polynucleotide. The reporter molecules are shown in their expected binding configuration, where substantially every phosphodiester linkage is paired with a reporter cation, and the reporter molecules are arrayed head-to-head and tail-to-tail. Assuming a maximum density of bound reporter molecules, it can be appreciated that an N-base analyte can bind up to about N/2 reporter molecules. More generally, depending on the size of analyte and the relative number of both reporter moieties and cationic groups per reporter, the assay method readily leads to binding of thousands to several hundred thousand or more reporter molecules to each reagent-bound analyte molecule. The sensitivity of detection can therefore be between 2 and 4 orders of magnitude greater than in existing types of polynucleotide-based diagnostics, where analyte detection is generally based on one or a few probe molecules per analyte molecule, with each probe typically containing several dozen reporter moieties.

After reaction with the reporter solution, typically at room temperature for 1-2 minutes, the reagent is washed to remove unbound reporter, and then can be assessed directly for bound reporter. In determining the amount of reporter associated with the reagent, it may be desirable, particularly in the case of fluorescent or chromophoric reporter groups, to elute the reporter from the reagent with a high salt solution and then assess the eluate for reporter. Alternatively, the reporter/analyte complex can be eluted from the reagent with a solution capable of disrupting Watson/Crick bonds, such as formamide, and then the reporter in the eluted complex is assessed. Other types of reporter groups, such as enzymes, can be readily assessed with the reporters either bound to or eluted from the reagent. Methods for determination of a variety of different reporter groups, such as those mentioned above, are well known. Examples 31 and 32 illustrate diagnostic procedures based on determination of fluorescent and enzymatic reporters, respectively.

From the foregoing, it can be appreciated how various objects and features of the invention are met. The diagnostic reagent can be readily tailored, by reagent polymer design, for the detection of any ribo- or deoxyribopolynucleotide having a unique base sequence. Further, the reagent polymer can be tailored to bind a given target sequence with high sequence specificity at a convenient temperature.

For detection of duplex polynucleotides, the reaction can be carried out under low-salt and/or denaturing conditions which prevent competition from complementary polynucleotide strands for reagent binding to the analyte. This diagnostic system therefore provides the advantage of the prior art solid-support, single-probe poly nucleotide diagnostic system, in that competition between complementary strands is eliminated, but avoids the rather laborious step associated with that system in attaching single-strand test nucleic acids to the solid support. At the same time, the system avoids the problems associated with the dual-probe polynucleotide diagnostic system described earlier, in that analyte detection is based on pseudo-first order kinetics, and only one sequence-specific binding polymer is required.

According to another important feature of the invention, reporter binding to the analyte is based on sequence-independent electrostatic interactions rather than sequence-specific binding, as in existing types of polynucleotide diagnostics. Accordingly, the reporter itself can be prepared relatively cheaply, can react with the analyte quickly and under a wide range of conditions, and, most importantly, can bind to the analyte at a density ranging up to multiple reporter moieties per polynucleotide subunit in the analyte. Accordingly, the sensitivity of the diagnostic system can be in the range of 2 to 4 or more orders of magnitude greater than existing tests, which rely on detection of one or a few probes, containing a limited number of reporter moieties, per analyte molecule.

The following examples illustrate preparation and use of assay systems constructed according to particular embodiments of the invention, but are in no way intended to limit the scope of the invention.

EXAMPLES

Examples 1 through 9 illustrate preparation of the subunits required for synthesis of the preferred embodiments of the polynucleotide-binding polymers. Examples 10 through 14 illustrate procedures for joining these subunits via uncharged achiral linkages. Examples 15 through 19 demonstrate preferred methods for assembling the subunits into polynucleotide-binding polymers, and Examples 20 through 22, methods for attaching the binding polymers to solid supports to produce the desired diagnostic reagents. Examples 23 through 30 detail the preparation of various polycationic reporters. Examples 31 and 32 illustrate use of the various components of the diagnostic system for the detection of specific polynucleotide analytes.

These particular embodiments of the invention are in no way intended to limit the scope of the invention.

EXAMPLE 1

Preparation of ribonucleosides and deoxyribonucleosides

The following nucleosides are obtained from Sigma Chemical Co. St. Louis, Mo.: deoxyuridine, deoxyguanosine, thymidine, deoxyadenosine, deoxycytidine, 5-bromodeoxyuridine, deoxyinosine, 2,6-diamino-9-(2-deoxy-β-D-erythro-pentofuranosyl)9H-purine (2,6-diaminopurine deoxyriboside), uridine, guanosine, 5-methyluridine, adenosine, cytidine, 5-bromouridine, inosine.

2,6-Diamino-9-(β-D-ribofuranosyl)-9H-purine (2,6-diaminopurine riboside) is obtained from Pfaltz and Bauer, Inc., Division of Aceto Chemical Co., Inc. Waterbury. Conn.

The following nucleosides are prepared by the literature methods indicated:

1-(2-Deoxy-β-D-erythro-pentofuranosyl)-2-pyrimidinone (2-hydroxypyrimidine deoxyriboside) is prepared by the method of P. Kohler, E. Volz, U. Seguin, and C. Tamm in *Nucleic Acid Chemistry* (L. B. Townsend and R. S. Tipson, eds) John Wiley and Sons, Inc. (1976).

1-(2-Deoxy-β-D-erythro-Pentofuranosyl)-4-methoxy-2-pyrimidinone is prepared by the following procedure:

1-(3',5'-Di-O-benzoyl-2-deoxy-β-D-erythro-pentofuranosyl)-4-methylthio-2-pyrimidinone (prepared as in D. Cech and A. Holy, *Collection of Czechoslov Chem Comm* (1977) 42:2246) is treated with 200 ml of 0.2M sodium methoxide solution. The resulting solution is allowed to stand overnight at room temperature. This solution is then neutralized with Dowex 50X8 (H+ form) and filtered; the residue is dissolved in water (100 ml) extracted with ether (2.50 ml) and the aqueous phase evaporated. The residue is an amorphous material which is used directly in succeeding reactions.

2-Amino-9-(2-deoxy-β-D-erythro-Pentofuranosyl) 1,9-dihydro-6H-purine-6-thione (deoxythioguanosine) is prepared by the procedure of R. H. Iwamoto, E. M. Acton, and L. Goodman *J Med Chem* (1963) 6:684.

1-(β-D-Ribofuranosyl)-2-pyrimidinone (2-hydroxypyrimidine riboside) is prepared by the procedure of U. Niedballa and H. Vorbruggen, *J Org Chem* (1974) 39:3668.

1-(2-Deoxy-β-D-ribofuranosyl)-4-methoxy-2-pyrimidinone (2-hydroxypyrimidine deoxyriboside) is prepared by the procedure of R. Wightman and D. Holy, *Collection of Czechoslov Chem Comm* (1973) 38:1381.

2-Amino-9-(β-D-ribofuranosyl)-1,6-dihydro-6H-purine-6-thione (thioguanosine) is prepared by the procedure of J. J. Fox, I. Wempen, A. Hampton and I. L. Doerr, *J Amer Chem Soc* (1958) 80:1669.

EXAMPLE 2

Preparation of Base-Protected Nucleosides

Dimethoxytrityl chloride, N-benzoyladenosine, N-benzoyl-2'-deoxyadenosine, N-benzoylcytidine, N-benzoyl-2'-deoxycytidine and N-isobutyryl-2'-deoxyguanosine are obtained from Sigma Chemicals. St. Louis, Mo. 9-Fluorenylmethoxycarbonyl chloride (FMOC chloride), trimethylchlorosilane, isobutyric anhydride, 4-nitrobenzoyl chloride and all organic solvents for reactions and chromatography are obtained from Aldrich Chemical Co., Milwaukee, Wis. Silica Gel is obtained from EM Science, Cherry Hill, N.J.

2.1 Guanosine

The N-2 9-fluorenylmethoxycarbonyl derivative is prepared by the procedure below which is general for the protection of nucleoside amino groups:

Guanosine (1 mmol) is suspended in pyridine (5 ml) and treated with trimethylchlorosilane (5 mmol). After the solution is stirred for 15 minutes 9-fluorenylmethoxycarbonyl chloride (5 mmol) is added and the solution maintained at room temperature for 3 hours. The reaction is cooled in an ice bath and water (1 ml) is added. After stirring for 5 minutes conc. ammonia (1 ml) is added and the reaction stirred for 15 minutes. The solution is evaporated to near dryness and the residue dissolved in chloroform (10 ml). This solution is washed with sodium bicarbonate solution (5 ml, 10%), dried over sodium sulfate and evaporated. The residue is coevaporated several times with toluene and the product chromatographed on silica gel using a gradient of methanol (0–50%) in methylene chloride.

N-Isobutyrylguanosine is prepared by the method of Letsinger and Miller, *J Amer Chem Soc* (1969) 91:3356.

N-2 Acetylguanosine is obtained by the method of C. B. Reese and R. S. Saffhill, *J Chem Soc Perkin Trans* (1972) 1:2937.

2.2 Deoxyguanosine

The N-2 9-fluorenylmethoxycarbonyl derivative is prepared by the method of J. Heikkla and J. Chattopadhyaya, *Acta Chem Scand* (1983) B37:263.

The N-2 acetyl derivative is obtained from Research Plus Inc., Bayonne. N.J.

The N-2 phenylacetyl derivative is prepared by the method of Benseler and McLaughlin, *Synthesis* (1986) 12:45.

2.3 Deoxyadenosine

The N-6 2 (4-nitrophenyl)-ethoxycarbonyl derivative is prepared by the method of F. Himmelsbach and W. Pfleiderer, *Tetrahedron Lett* (1983) 24:3583.

N-6 4-Nitrobenzoyl-2'-deoxyadenosine is prepared using the procedure above for FMOC-guanosine except that 4-nitrobenzoyl chloride is substituted for FMOC chloride.

The N-6 2-(phenylsulfonyl)-ethoxycarbonyl derivative is prepared by the procedure for FMOC guanosine except the 2-(phenylsulfonyl)-ethyl chloroformate (obtained from N. Balgobin, S. Josephson and B. Chattopadhyaya, *Tetrahedron Lett* (1981) 22: 3667) is used as the acylating agent and N-methylimidazole or pyridine is used as the solvent.

2.4 Adenosine

The N-6 2-(4-nitrophenyl)-ethoxycarbonyl derivative is prepared by the method of F. Himmelsbach and W. Pfleiderer, *Tetrahedron Lett* (1983) 24:3583.

N-6 4-Nitrobenzoyladenosine is prepared using the procedure above for FMOC-guanosine except that 4-nitrobenzoyl chloride is substituted for FMOC chloride.

The N-6 2-(phenylsulfonyl)-ethoxycarbonyl derivative is prepared by the procedure for FMOC guanosine except the 2-(phenylsulfonyl)-ethyl chloroformate (obtained from N. Balgobin, S. Josephson and B. Chattopadhyaya *Tetrahedron Lett* (1981) 22:3667) is used as the acylating agent and N-methylimidazole or pyridine is used as the solvent.

2.5 Deoxycytidine

The N-4 2-(4-nitrophenyl)-ethoxycarbonyl derivative is prepared by the method of F. Himmelsbach and W. Pfleiderer, *Tetrahedron Lett* (1983) 24:3583.

The N-6 2-(phenylsulfonyl)-ethoxycarbonyl derivative is prepared by the procedure for FMOC guanosine except the 2-(phenylsulfonyl)-ethyl chloroformate (obtained from N. Balgobin, S. Josephson and B. Chattopadhyaya *Tetrahedron Lett* (1981) 22:3667) is used as the acylating agent and N-methylimidazole or pyridine is used as the solvent.

2.6 Cytidine

The N-4 2-(4-nitrophenyl)-ethoxycarbonyl derivative is prepared by the method of F. Himmelsbach and W. Pfleiderer, *Tetrahedron Lett* (1983) 24:3583.

The N-6 2-(phenylsulfonyl)-ethoxycarbonyl derivative is prepared by the procedure for FMOC guanosine except the 2-(phenylsulfonyl)-ethyl chloroformate (obtained from N. Balgobin, S. Josephson and B. Chattopadhyaya *Tetrahedron Lett* (1981) 22:3667) is used as the acylating agent and N-methylimidazole or pyridine is used as the solvent.

2.7 2,6-diaminopurine riboside

The N-2,N-6-bis(9-fluorenylmethoxycarbonyl) derivative of 2,6-diaminopurine riboside is prepared by the general procedure.

The N-2,N-6-bis(isobutyryl) derivative is prepared by the general procedure.

2.8 2,6-diaminopurine-2'-deoxyriboside

The bis N-2,N-6-(9-fluorenylmethoxycarbonyl) derivative of 2,6-diaminopurine-2'-deoxyriboside is prepared by the general procedure.

2.9 Thioguanosine

The N-2 9-fluorenylmethoxycarbonyl derivative of thioguanosine is prepared by the general procedure.

2.10 2'-Deoxythioguanosine

The N-2 9-fluorenylmethoxycarbonyl derivative of 2'-deoxythioguanosine is prepared by the general procedure.

EXAMPLE 3

Preparation of 5'-amino-2',5'-dideoxyribonucleoside subunits

Carbon tetrabromide, sodium azide, p-toluenesulfonyl chloride (tosyl chloride), triphenyl phosphine and 10% palladium on carbon are purchased from Aldrich Chem Co. Lithium azide is obtained from Kodak Laboratory and Specialty Chemicals.

3.1 General Method

The nucleosides employed in this example are thymidine, N6-benzoyl-2'-deoxyadenosine, N4-benzoyl-2'-deoxycytodine, and 2'-deoxyinosine, 2-hydroxy-pyrimidine-2'-deoxyriboside and the N2-N6-bisisobutyryl derivative of 2,6-diamino purine-2'-deoxyriboside (see Example 1). The required dried nucleoside (1 mmol) is weighed into a reaction vessel containing triphenyl phosphine (1.01 mmol) and lithium azide (5 mmol). After the solids are suspended in DMF, carbon tetrabromide (1.0 mmol) is added to the vessel. The solution is stirred at room temperature for 24 h. After quenching the reaction with methanol, the solution is evaporated to dryness. The residue is chromatographed on silica gel eluting with methanol/chloroform mixtures to afford the desired 5'-azido-2',5'-deoxynucleoside.

The 5'-azido nucleoside (1 mmol) is dissolved in ethanol. Hydrogenation in the presence of 10% palladium on carbon (catalytic amount) under a hydrogen atmosphere (35 psi) occurs over 10 h. The solution is filtered and evaporation under reduced pressure affords a crude solid. The solid is purified by trituration with the appropriate solvent. For the case of base-protected nucleosides, yields in this step can be significantly improved by carrying out the reduction in the presence of sufficient acetic acid to protonate the newly formed 5'-amino group. The presence of DMF as cosolvent is also advantageous. Yields are also improved if 1 equivalent of p-toluene sulfonic acid is added prior to evaporation.

3.2 5'-Azidouridine derivativ

The 5'-azido derivative of 5-bromo-2'-deoxy uridine is prepared via the method described above. The 5'-azido-5-bromo-2'-deoxyuridine (1 mmol) is treated with triphenyl phosphine (1.5 mmol) in pyridine at room temperature for 2 h. Concentrated ammonia (1 ml) is added to the reaction vessel. After 14 h the solvent is removed under vacuum. The residue is dissolved in THF and this solution is added to hexanes. The precipitate is collected and the solid triturated with the appropriate solvent to afford the 5'-amino-5-bromo-2'-deoxyuridine.

3.5 5'-Azido guanosine

An alternate preparation of 5'-amino-2',5'-dideoxyguanosine (or 5'-amino-2',5'-dideoxyinosine) is to treat the protected 2'-deoxy guanosine (protected as the N-2-acetyl, the N-2-phenylacetyl, or the N-2-FMOC derivative) (1 mmol) with tosyl chloride (1.3 mmol) in pyridine at 0° C. overnight. The solution is evaporated to dryness and the residue is dissolved in chloroform. The resulting solution is washed twice with aqueous sodium bicarbonate and dried over sodium sulfate. The solvent is evaporated and the residue chromatographed on silica gel eluting with methanol/chloroform mixtures. The resulting tosylate (1 mmol) is treated with sodium azide (6 mmol) in DMF at 80°–100° C. for a few h, or lithium azide (10 mmol) in DMF at 60° C. for several h. The solvent is removed by rotovap and the residue is chromatographed on silica gel eluting with chloroform/methanol solvent mixtures. The azide is reduced to the desired amine using the above procedure.

Alternate protecting groups for the base nitrogens of 2'-deoxycytidine, 2'-deoxyadenosine, 2'-deoxyguanosine, and 2,6-diaminopurinedeoxyriboside are 2-(phenylsulfonyl)ethoxycarbonyl for 2'-deoxycytidine and 2'-deoxyadenosine and the use of the 9'-fluorenylmethoxycarbonyl (FMOC) to protect 2'-deoxyguanosine and 2,6-diaminopurine deoxyriboside, as in Example 2.

EXAMPLE 4

Preparation of 3'-amino-2',3'-dideoxyribonucleoside subunits

Thymidine is transformed to 5'-O-acetyl-3'-azido-2',3'-dideoxythymidine and this is converted to 3'-azido-2',3'-dideoxyadenosine and 3'-azido-2',3'-dideoxyguanosine via the methods of M. Imazawa and F. Eckstein, *J Org Chem* (1978) 43:3044. The base moiety of the 3'-azidoadenosine is protected as either the benzoyl or the 2-(phenylsulfonyl)ethoxycarbonyl derivative (as shown in Example 1). N-2 of the 3'-azidoguanosine is protected as either the acetyl or FMOC derivative (see Example 1). The reduction of these 3'-azido functions to the 3'-amino-2',3'-dideoxyribonucleosides is performed as shown in Example 3.

EXAMPLE 5

Preparation of morpholino-type subunits derived from ribonucleosides

Ammonium biborate sodium m-periodate sodium cyanoborohydride, uridine, N4-benzoyl cytidine, and N6-benzoyl adenosine are obtained from Sigma Chemical Co. N2-isobutyryl guanosine is prepared by the general method of Letsinger and Miller (*J Amer Chem Soc* (1969) 91:3356). Trityl chloride, 2-phenyl-2-propanol, and bis(p-nitrophenyl) carbonate are obtained from Aldrich Chemical Co.

The morpholino derivative of uridine is prepared by dissolving 1 mmol of uridine Plus 2 mmol of ammonium biborate, $(NH_4)_2B_2O_7$, in 5 ml of water. While stirring in an ice bath protected from direct light 1.2 mmol of sodium m-periodate in 5 ml of water is added. After 90 min, 0.2 ml of 1,2-propanediol is added and stirring is continued for 10 min at rt. Thereafter, while stirring in a well-ventilated hood, 0.25 g of sodium cyanoborohydride dissolved in 3 ml of water is added and the mixture stirred for 4 hr at rt. Thereafter, the reaction mixture is preferably adjusted to pH 5.5 with acetic acid or toluene sulfonic acid and then reduced to an oil under vacuum in a warm water bath, resuspended in a minimal volume of methanol, layered on a silica gel chromatography column, and the column eluted with methanol/1% triethylamine. The morpholino product elutes from the column as a sharp band moving significantly slower than the original ribonucleoside and its oxidation products. The morpholino product has a UV spectrum essentially identical to the parent ribonucleoside, but its mass is lower by 17 daltons (determined by mass spectral analysis using fast atom bombardment).

The morpholino nitrogen (3′) is next protected by reacting the product with 2-phenylisopropyl phenyl carbonate. The required active carbonate is prepared and reacted with the morpholino subunit essentially by the methods of Sandberg and Ragmarsson (*Int J Peptide Protein Res* (1974) 6:111). Alternatively, it is more convenient to protect the morpholino nitrogen by reacting with trityl chloride in the presence of diisopropylethylamine. Finally, if desired (depending on the method to be used for subunit assembly into polymers) the hydroxyl at the position corresponding to the original 5′ (now referred to as the 6′) can be activated by dissolving the N-protected subunit in a minimal volume of dry dimethylformamide and adding 2 equivalents of triethylamine, N-methylimidazole, or N,N-dimethylamino pyridine. After 3 h at rt, the reactions mixture is reduced in volume under vacuum in a warm water bath. The thick syrup is resuspended in a small volume of dichloromethane and layered on a silica gel column, which is subsequently eluted with a mixture of dichloromethane/ether (1:1 by vol) 0.2% in N,N-dimethylaniline by volume. With this solvent system, the activated product moves substantially slower than p-nitrophenol and bis(p-nitrophenyl)carbonate but much faster than the unreacted starting material. The activated product is readily visualized on silica gel TLC plates simply by exposing to ammonia fumes, whereupon a yellow nitrophenolate ion is generated within one to two minutes.

Other ribonucleosides (bases protected where necessary as in Example 2) are converted to their corresponding morpholino derivatives by essentially the same methods—though varying amounts of methanol must be added to effect dissolution of the protected ribonucleosides before the initial periodate oxidation step.

When the morpholino-type subunits are to be coupled via thiocarbamate linkages, the preferred base-protective groups for the common starting ribonucleosides are: the phenylsulfonylethoxycarbonyl moiety for cytidine and adenosine and the 9-fluorenyl methoxycarbonyl moiety for guanosine.

EXAMPLE 6

Preparation of Purine and Pyrimidine Pyrrolidones

Potassium t-butoxide, anisoyl chloride, 6-chloropurine, 10% palladium on charcoal, phthaloyl chloride, 2-amino-6-chloropurine, 20% aqueous tetraethylammonium hydroxide, 25% aqueous trimethylamine, 2-pyrimidinone, N-bromosuccinimide, trifluoroacetic acid, 4-nitrophenol, and N,N-disuccinimydyl carbonate are obtained from Aldrich. Lithium azide is obtained from Eastman Kodak, Rochester, N.Y. C18 reverse phase silica gel is obtained from Whatman, Hillsboro, Oreg.

6.1 Preparation of (S)-5-[(4-amino-2-oxopyrimidinyl)methyl]-pyrrolidone (henceforth referred to as the cytosine pyrrolidone)

Cytosine (2.2 mmol) is dissolved in dimethyl sulfoxide (2 ml) which contains potassium tert-butoxide (2 mmol). This solution is added to a flask which contains (S)-5-(tosyloxymethyl)-2-pyrrolidone (1 mmol, prepared by the procedure of E. Hardegger and H. Ott, *Helv Chim Acta* (1955) 38:312). After dissolution, the mixture is stirred at 25° C. for 6 h. The mixture is neutralized with acetic acid (2 mmol) and evaporated under reduced pressure. The residue is taken up in dimethyl formamide (5 ml) and evaporated under reduced pressure, and this procedure repeated three times.

6.2 preparation of N-4 anisoylcytosine pyrrolidone

The mixture from the previous paragraph is dissolved in pyridine or N-methylimidazole (10 ml) and treated with anisoyl chloride (2.8 mmol) at room temperature. After stirring for 2 h, the mixture is quenched with ice (0.5 g). After 5 min, 1 ml of 29% ammonia was added. After 15 min at rt the solution is dissolved in ethyl acetate (15 ml) and washed twice with brine (15 ml). The washings are combined and washed with ethyl acetate (2×30 ml). the combined organic layers dried with sodium sulfate and evaporated under reduced pressure. The residue is coevaporated several times with toluene and the residue chromatographed on silica gel with a gradient of methanol in methylene chloride (0–20%).

6.3 Preparation of 6-chloropurine pyrrolidone

This compound is prepared as for the alkylation of cytosine except that the alkylation is performed on 6-chloropurine and the mixture was heated at 35°-95° C. for several h. The mixture is cooled to room temperature, neutralized with acetic acid (2 mmol) and evaporated under reduced pressure, shaken with a mixture of 20% methanol/chloroform and 10% sodium bicarbonate. The aqueous layer is washed with chloroform the combined organic layers are dried over sodium sulfate and evaporated under reduced pressure. The residue is chromatographed on silica gel using a gradient of methanol in chloroform (0–25%).

6.4 Preparation of 6-azidopurine pyrrolidone

The 6-chloropurine pyrrolidone (1 mmol) is treated with lithium azide (2 mmol) in dimethyl sulfoxide (2 ml) at 30°–100° C. for several h. At the end of this time the mixture is evaporated under reduced pressure, dissolved in chloroform, washed with 10% sodium bicarbonate, and the organic layer dried over sodium sulfate and concentrated under reduced pressure. The residue is chromatographed on silica using a gradient of methanol in chloroform (0–25%).

6.5 Preparation of adenosine pyrrolidone

The azide from the previous example is hydrogenated by shaking the azide (1 mmol) with 30 pounds of hydrogen pressure in a solution of ethanol (10 ml) containing palladium on charcoal (100 mg, 10% by weight Pd) for 24 h. The solution is filtered through celite and the solvent evaporated. The residue is used directly for the next step.

6.6 Preparation of N-6 phthaloyladenosine pyrrolidone

The phthaloyl group is introduced at the N-6 position by the acylation of the adenosine pyrrolidone (1 mmol) with phthaloyl chloride (1.4 mmol) using the procedure above for the anisoylation of cytidine except that no ammonia was added in the workup.

6.7 Preparation of 2-amino-6-chloropurine pyrrolidone

The pyrrolidone tosylate is alkylated with 2-amino-6-chloropurine as per the preparation of the 6-chloropurine derivative.

6.8 Preparation of guanine pyrrolidone

The chloropurine pyrrolidone (1 mmol) from the previous paragraph is dissolved in diglyme (10 ml) and 25% aqueous trimethylamine (2 ml). The solution is stirred at rt for 5 h, water (10 ml) is added, and the mixture concentrated to 10 ml under reduced pressure. Acetic acid (2 ml) is added, and the mixture was evaporated under reduced pressure to an oil. The residue which contains trimethylammonium acetate is used directly for the next step.

6.9 Preparation of N-2 acetylguanine pyrrolidone

Guanine pyrrolidone (1 mmol) from the previous paragraph is reacted with acetic anhydride (5 ml) at reflux for 2 h. The solvent is evaporated and the residue coevaporated with dimethylformamide. The residue is dissolved in methanol (5 ml) saturated with ammonia at 0° C., and the solution is stirred for 2 h at this temperature. The solvent is evaporated under reduced pressure and the residue purified by chromatography on a short column of silica using a gradient of methanol in chloroform (5–50%).

6.10 Preparation of 2-amino-6-azidopurine pyrrolidone

This compound is prepared from the 2-amino-6-chloropurine pyrrolidone by use of the procedure of Example 7.4, except that the reaction requires longer times and was performed at a higher temperature.

6.11 Preparation of 2,6-diaminopurine pyrrolidone

This compound is prepared as for the adenosine pyrrolidone by reduction of the 2-amino-6-azido derivative.

6.12 Preparation of N-2 acetyl N-6 phthaloyl 2,6-diamino purine pyrrolidone

The acetyl group is introduced by the method above for N-2 acetylguanine pyrrolidone except that the methanolic ammonia treatment is carried out for 8 h. The solvents are evaporated and the residue is phthaloylated as for the adenosine derivative.

6.13 preparation of inosine pyrrolidone

6-Chloropurine pyrrolidone (1 mmol) was converted to the inosine derivative by the method used for the preparation of the guanine pyrrolidone derivative. The compound is purified by chromatography on silica using a gradient of methanol (5–25%) in chloroform.

6.14 Preparation of 2-hydroxypyrimidine pyrrolidone

This compound is obtained by the alkylation of 2-pyrimidinone by the procedure used for the preparation of the 6-chloropurine derivative.

EXAMPLE 7

Preparation of Purine and Pyrimidine T-BOC Amino Acids

The general procedure described below for the cytosine pyrrolidone may be applied to all properly protected pyrrolidone derivatives. The product, referred to as the t-BOC acid is formed by cleavage of the pyrrolidone ring to an acid and a t-BOC amine.

7.1 Preparation of the cytosine t-BOC acid

N-4-Anisoylcytosine pyrrolidone (1 mmol) is dissolved in methylene chloride (0.5M solution) containing di-tert-butyl dicarbonate (2 mmol). triethylamine (1 mmol). and dimethylaminopyridine (1 mmol). The solution is stirred for 10 h at rt. The volatiles are removed and the residue purified on silica using a gradient of methanol in chloroform (0–20%). The residue is dissolved in tetrahydrofuran (0.2M solution) to which is then added lithium hydroxide ( 3 mmol, as a 1M solution). After 5 h at rt, the solution is neutralized by the addition of 10% acetic acid (3 mmol) and the solvents removed under reduced pressure. The residue was dissolved in 9N ammonia and stirred at room temperature for 1–10 h. The solvent is removed under reduced pressure and the residue purified by chromatography on C18 reverse phase silica gel using water and methanol (or trifluoroethanol) mixtures.

7.2 Preparation of uracil t-BOC acid

This is prepared from the cytosine t-BOC acid by the following procedure:

The cytosine t-BOC acid (1 mmol) is dissolved in aqueous acetic acid and treated with sodium nitrite (1 mmol) at 4° C. The mixture is stirred for 1 h and evaporated to dryness under reduced pressure. The product is purified by chromatography in C18 reverse phase silica gel using water and methanol (or trifluoroethanol) mixtures.

7.3 Preparation of 5-bromouracil t-BOC acid

This compound is obtained from the uracil t-BOC acid by the following procedure:

The uracil t-BOC acid (1 mmol) is dissolved in DMF (3 ml) and treated with N-bromosuccinimide (1.2 mmol). The solution is allowed to stand at room temperature for 16 h. After removal of the solvents under reduced pressure the product is purified by chromatography on C18 reverse phase silica gel using water and methanol (or trifluoroethanol) mixtures.

7.4 Preparation of N-protected t-BOC acid

This general procedure for acylating the exocyclic amino groups of the recognition moiety is also applicable to the protection of the adenosine derivative.

The cytosine t-BOC acid (1 mmol) from the previous paragraph is dissolved in N-methylimidazole or pyridine (5 ml). After 15 min at room temperature the solution is treated with 2-(4-nitrophenyl)ethylchloroformate (3 mmol, obtained from F. Himmelsbach and W. Pfleiderer, *Tetrahedron Lett* (1983) 24:3583). The reaction is maintained at room temperature for 8 h, then cooled in an ice bath, and water (1 ml) was added. After 5 min, 1 ml of concentrated ammonia is added and the mixture stirred at rt for 15 min. The reaction is then evaporated to dryness and the residue dissolved in water. The solution is made acidic with 2M HCl and extracted with chloroform. The combined organic extracts are dried over sodium sulfate and evaporated under reduced pressure. The residue is purified by chromatography on silica using a gradient of methanol in chloroform (5–50%).

For protection of the guanine and 2,6-diaminopurine derivatives, the above procedure was modified so that the reaction was carried out in pyridine and the acylating agent was 9-fluorenylmethyl chloroformate.

EXAMPLE 8

Preparation of Purine and Pyrimidine Amino Acids

The following procedure is applicable to all the derivatives. It removes the t-BOC group and frees the primary amino group of the backbone.

The t-BOC acid (1 mmol) was dissolved in 20% trifluoroacetic acid in methylene chloride (5 ml) and stirred at rt for 30 min. Toluene (3 ml) is added and the solvents are evaporated under reduced pressure to give the amino acid trifluoroacetate salt. This is used directly for coupling reactions.

EXAMPLE 9

Preparation of 5'-protected, 3'-activated 2'-deoxynucleosides.

9.1 2'-deoxyribonucleoside 5'-O-dimethoxytrityl derivatives

The procedure below is general for the preparation of 2'-deoxyribonucleoside 5'-O-dimethoxytrityl derivatives:

N-2 9-Fluorenylmethoxycarbonyl-2'-deoxyguanosine (1 mmol) is dissolved in anhydrous pyridine (2.0 ml) and kept at 0° C. Dimethoxytrityl chloride (1.2 mmol) is added in portions (0.15 mmol) during an 8 hour period. After an additional 2 hours methanol (0.5 ml) was added and the solution is concentrated at reduced pressure. The residue is treated with a mixture of sodium bicarbonate (2 ml. 5%) and methylene chloride (5 ml).

The aqueous layer is extracted with methylene chloride (2×5 ml) and the combined organic layers are dried over sodium sulfate and evaporated. The residue is coevaporated several times with toluene and the product is purified by chromatography on silica gel using a gradient of methanol in methylene chloride (0–10%).

9.2 5'-O-dimethoxytrityl-2'-deoxyribonucleoside 3'-O-(4-nitrophenyl)carbonates.

The preparation of 5'-O-dimethoxytrityl-2-deoxycytidine 3'-O-(4-nitrophenyl)carbonates is described in the following procedure which is general for the preparation of the 4-nitrophenylcarbonates. Bis (4-nitrophenyl)carbonate and N,N-dimethylaminopyridine are obtained from Sigma.

5'O-Dimethoxytrityl-N-2-(4-nitrophenyl)ethoxycarbonyl-2'-deoxycytidine (1 mmol) is dissolved in anhydrous dimethylformamide (5 ml) at room temperature and treated with bis(4-nitrophenyl)carbonate (2 mmol) and then evaporated under reduced pressure. The residue is dissolved in dimethylformamide (5 ml) and N,N-dimethylaminopyridine (0.1 mmol) is added. The yellow solution is evaporated and allowed to react for 1 h. The reaction mixture is dissolved in chloroform (10 ml) and washed with aqueous HCl (5 ml, 0.1M). The organic layer is washed twice with aqueous NaOH (5 ml, 0.1M), water (2 ml), dried over sodium sulfate and evaporated. The residue is applied to a silica gel column and eluted with a gradient of isopropanol in chloroform (0–10%). The fractions containing the product are pooled, evaporated, dissolved in chloroform (10 ml) and the aqueous NaOH washes are repeated to remove traces of 4-nitrophenol. The organic layer is washed with water, dried over sodium sulfate and evaporated. The product is homogeneous by TLC and is used directly for preparation of the dimeric carbonates.

For the preparations of the carbonates of nucleosides containing the FMOC group it is sometimes advantageous to use N-methylimidazole as the catalyst rather than N,N-dimethylaminopyridine.

EXAMPLE 10

Formation of a carbonate intersubunit linkage.

The preparation of cytidinyl-(3'–5')-cytidine carbonate is described in the procedures below. This is a general procedure for the formation of the carbonate intersubunit linkage and the deprotection of the oligocarbonate. Note that the base protecting groups must be 2-(4-nitrophenyl)ethoxycarbonyl, 2-(phenyl sulfonyl)ethoxycarbonyl, or FMOC. Tert-butyl dimethylsilyl chloride is obtained from Aldrich.

10.1 Preparation of 2'-deoxynucleoside 3'-O-tert-butyldimethylsilyl derivatives.

The preparation of 3'-O-tert-butyldimethylsilyl-N-2-(4-nitrophenyl)ethoxycarbonyl-2'-deoxycytidine is described in the following procedure which is a general procedure for the preparation of 2'-deoxynucleoside-3'-O-tert-butyldimethylsilyl derivatives:

To a stirred solution of 5'-O-dimethoxytrityl-N-4-(4-nitrophenyl)-ethoxycarbonyl-2'-deoxycytidine (1 mmol) and imidazole (3.5 mmol) in dry dimethylformamide or tetrahydrofuran (10 ml) is added dropwise a solution of tert-butyldimethylsilyl chloride (3 mmol) in dry DMF (10 ml). The reaction is stirred for 1 h, quenched with ice, extracted with methylene chloride, washed with water and dried over sodium sulfate. The organic layer is evaporated to dryness under reduced pressure and purified by chromatography over silica gel with methylene chloride as eluant.

To a solution of the 5'-O-dimethoxytrityl derivative from the Previous paragraph (1 mmol) in methylene chloride (5 mmol) is added a solution of zinc bromide in methylene chloride (10 ml, 1M) containing methanol (15% v/v). The reaction mixture is stirred for 30 min, quenched with ice, and extracted with methylene chloride. The organic layer is washed with water, dried over sodium sulfate, and evaporated to dryness under reduced pressure. The product is purified by chromatography over silica gel using a gradient of methanol (0–10%) in methylene chloride.

5'-O-dimethoxytrityl-N-2-(4-nitrophenyl)ethoxy carbonyl-2'-deoxycytidine-3'-O-(4-nitrophenyl)carbonate (1.5 mmol) and 3'-O-tert-butyldimethylsilyl-N-4-(4-nitrophenyl)ethoxycarbonyl-2'-deoxycytidine (1 mmol) are dissolved in dimethylformamide (5 ml) and the solvent removed under reduced pressure. This is repeated two times. The residue is redissolved in dimethylformamide (5 ml) and treated with N,N-dimethylaminopyridine (0.5 mmol) or N-methylimidazole (1 mmol). The solvent is removed by evaporation under reduced pressure and the reaction allowed to sit overnight at rt. The residue is dissolved in chloroform (20 ml) and washed with aqueous HCl (2 ml, 0.1M), water (2 ml). aqueous NaOH (2×2 ml, 0.2M), water (2 ml). and the organic layer dried over sodium sulfate and evaporated. The residue is purified on silica gel using a gradient of isopropanol in chloroform (0–30%). The isolated product is homogeneous on TLC and by 400 MHz NMR.

The residue is desilylated by using the 2M HF/1M tert-butylammonium fluoride (TBAF) reagent described in B. L. Gaffney and R. A. Jones, *Tetrahedron Lett* (1982) 23:2257. To the 2M HF/1M tert-butylammonium fluoride in pyridine (1 mmol of TBAF) is added the deprotected nucleoside from the previous paragraph. After stirring for 24 h, the reaction is partitioned between methylene chloride and aqueous sodium bicarbonate. The organic layer is washed with water, dried over sodium sulfate, and evaporated to dryness. The residue is purified by chromatography on silica using a gradient of methanol in methylene chloride (5–25%).

The 3'-hydroxydinucleoside carbonates are converted to the 3'-(4-nitrophenyl)-carbonates by the method in Example 9. These derivatives may be reacted with the 5'-hydroxyl of a nucleoside or oligonucleoside carbonate to prepare higher order oligonucleoside carbonates.

EXAMPLE 11

Formation of a carbamate intersubunit linkage

Bis(p-nitrophenyl)carbonate, p-anisoyldiphenyl methyl chloride, N,N-dimethylaniline (DMA), and triethylamine are available from Aldrich Chemical Co.

The required 5'-amino-2',5'-dideoxyribonucleoside (employing acetyl, phenylacetyl, or benzoyl groups for base protection where necessary) (1 mmol) prepared in Example 3 above, is treated with p-anisoyl diphenylmethyl chloride (1.2 mmol) in pyridine containing 2.4 mmol of triethylamine. After 12 h the solvent is evaporated and the residue is redissolved in chloroform. This solution is washed once each with aqueous NaHCO$_3$ and water, then dried over Na$_2$SO$_4$. After evaporation of the solvent, the residue is chromatographed on silica gel eluting with chloroform/methanol/1% triethylamine mixtures.

The 5'-tritylated aminonucleoside (1 mmol) is evaporated twice from DMF, then treated with bis-(p-nitrophenyl)carbonate (2 mmol) in the presence of triethylamine (or N,N-dimethylaminopyridine, or N-methyl imidazole)(catalytic amount) using DMF as the solvent.

After 3 h, the solvent is evaporated and the residue dissolved in chloroform. This solution is washed twice with 0.01N aqueous NaOH, once with water, then dried over Na$_2$SO$_4$. The solvent is removed by rotovap and the residue is chromatographed on silica gel eluting first with a chloroform/0.1% DMA mixture, then with a chloroform/methanol/0.1% DMA solvent system. The appropriate fractions are combined and evaporated to dryness. The residue is dissolved in a minimum of THF and this solution is added to an excess of hexanes or hexane/toluene. The precipitated activated nucleoside is collected by filtration and dried under vacuum.

The required 5'-aminonucleoside or its toluene sulfonate salt (1.1 mmol), as prepared in Example 3 above, is twice evaporated from DMF. The activated nucleoside (1 mmol) is added to the reaction vessel and the solids are dissolved in DMF. The solution is concentrated to a small volume and allowed to stand overnight. If the amine salt is used in the coupling, 3 equivalents of triethylamine are added after concentration. The solvent is completely removed under vacuum and the resulting residue is dissolved in chloroform. This solution is twice washed with 0.01N aqueous sodium hydroxide, once with water, then dried over solid sodium sulfate. The solvent is removed by rotovap, and the residue is chromatographed on silica gel eluting with the appropriate methanol/chloroform/1% triethylamine solvent system. The fractions containing the dimer nucleoside are combined, then evaporated to dryness. The residue is dissolved in a minimum of THF and this solution is added to hexane or hexanol/toluene. The precipitate is collected and dried under vacuum.

EXAMPLE 12

Formation of a thiocarbamate intersubunit linkage

N,N-dimethylaminopyridine (DMAP) is purchased from Aldrich Chemical Co.

Formation of the thiocarbamate intersubunit linkage of the 5'-aminonucleosides prepared in Example 3 is achieved in the same manner as described above in Example 11 with the following alterations in procedure. The 5'-aminonucleosides employed have as base-protecting moieties either 2-(phenylsulfonyl)ethoxycarbonyl (for deoxycytidine and deoxyadenosine) or 9-FMOC (for guanosine and 2,6-diamino-2'-deoxyriboside) groups. The preparation of these molecules are described above (Example 3). Activation of the 5'-tritylaminonucleoside (1 mmol) is achieved with p-nitrophenylchlorothioformate (as prepared by G Hilgetag and r. Phillippson, *Monatsber Deut Akad Wiss Berlin* (1964) 6:897) (1.2 mmol) in the presence of triethylamine (2 mmol) and the DMAP (catalytic amount) in DMF. The coupling step employs this activated monomer (1 mmol) with the requisite 5'-aminonucleoside (1.1 mmol) using DMAP or N-methyl imidazole as catalyst and DMF as the solvent. In this aqueous workup of these steps, the 0.01N aqueous NaOH washes are omitted, employing in their place water washes.

EXAMPLE 13

Formation of carbamate and thiocarbamate intersubunit linkages between morpholino type subunits N-methylimidazole is purchased from Aldrich Chemical Co.

The requisite dry, N'-protected, 5'-free alcohol morpholino type nucleoside (employing acetyl or benzoyl groups for base protection where necessary) (1 mmol), prepared in Example 5 above is treated with bis-(p-nitrophenyl)carbonate and triethylamine (or DMAP or N-methylimidazole) (catalytic amount) in DMF under anhydrous conditions. The solution is stirred for 3 h, then evaporated to dryness. The residue is dissolved in chloroform and the solution is washed twice with 0.01N aqueous NaOH, once with water, then dried over $Na_2SO_4$. The solvent is removed by rotovap and the residue is chromatographed on silica gel eluting with an appropriate chloroform/isopropanol/0.1% DMA mixture. The fractions containing the desired activated nucleoside are combined, evaporated, and the resulting solid is dissolved in a minimum of THF. The THF solution is added to an excess of hexanes and the resulting precipitate is collected and dried.

The required 6'-free hydroxy, N'-free morpholino type nucleoside (bases protected where necessary) (1.1 mmol) is treated with the 3'-protected '-(p-nitrophenoxycarbonyl)morpholino subunit (1 mmol) in DMF. The volume of the reaction solution is reduced under vacuum to a small volume. If required, a catalytic amount of N-methylimidazole or triethylamine is added to the reaction vessel. The resulting solution is allowed to stand overnight at rt. The remaining solvent is evaporated, and the residue is dissolved in chloroform. The chloroform solution is washed twice with 0.01N aqueous NaOH, once with water, and then dried over $Na_2SO_4$. The solvent is removed by rotovap and the residue is chromatographed on silica gel eluting with chloroform/methanol solvent mixtures. The fractions containing the desired dimer are combined, then rotovaped to dryness. The residue is dissolved in a minimum of THF and the solution is added to an excess of hexanes. The precipitate is collected and dried under vacuum.

Morpholino subunits linked by thiocarbamate moieties are prepared as related above in this example with the following experimental alterations. The base-protecting groups are either 1-(phenylsulfonyl)ethoxy carbonyl (for deoxycytidine and deoxyadenosine) or 9-FMOC (for deoxyguanosine and 2,6-diamino-2'-deoxy riboside) groups. The preparation of these molecules is described above (Example 5). Activation of the N-protected morpholino nucleoside (1 mmol) is achieved with p-nitrophenylchlorothioformate (1.2 mmol) in the presence of triethylamine (2 mmol) and DMAP or N-methyl imidazole (catalytic amount) in DMF. The coupling step employs this activated monomer (1 mmol) with the requisite N'-free morpholino nucleoside (1.1 mmol) using DMAP or N-methyl imidazole as catalyst and DMF as the solvent while warming the solution to 35°–40° C. In the aqueous workup of these steps, the 0.01N aqueous NaOH washes are omitted, employing in their place water washes.

EXAMPLE 14

Formation of an amide-linked dimer

14.1 N-protected t-BOC p-nitrophenyl ester

The following two procedures prepare active esters for coupling of subunits. It is general for all the t-BOC (di-t-butyl dicarbonate) acid derivatives.

To a 0.2–0.5M solution of the t-BOC acid from Example 8.4 in ethyl acetate (or methylene chloride). p-nitrophenol is added in about 20% excess. The calculated amount of dicyclohexylcarbodiimide is added to the solution at 0° C. After 0.5 h the mixture is allowed to come to rt and was held there for 1 h. The dicyclohexylurea which separated is filtered and washed with solvent. The combined filtrate and washings are evaporated to dryness under reduced pressure. The ester may be used directly for coupling reactions or may be purified by short column chromatography on silica using an isopropanol-in-chloroform gradient (0–50%).

14.2 N-protected t-BOC N-hydroxysuccinimidoyl ester

To a solution of the t-BOC acid from Example 8.4 (1 mmol) in acetonitrile (5 ml) is added pyridine (1 mmol) and N,N'-disuccinimidyl carbonate (1 mmol). The solution is stirred at rt for 3 h. The solvents are removed under reduced pressure and the residue dissolved in chloroform, the organic phase washed with 0.1M HCl and water, dried over sodium sulfate, and evaporated to dryness. The esters are sufficiently pure to be used directly.

14.3 Formation of a t-BOC amide-linked dimer

A fully protected t-BOC N-hydroxysuccinimidoyl ester or p-nitrophenyl ester prepared as above (1 mmol) is dried by several coevaporations with dry dimethyl formamide. The deprotected amino acid trifluoroacetate salt from Example 8 (1 mmol) is treated similarly. The two components are separately dissolved in dry dimethylformamide (2 ml), mixed, and treated with diisopropylethylamine (1.0 mmol). The solution is stirred at room temperature for 1 h. The solvent is next removed by evaporation under reduced pressure, the residue dissolved in chloroform and washed with dilute HCl. The organic layer is dried over sodium sulfate, evaporated to dryness under reduced pressure, and the residue purified by chromatography on silica gel using a gradient of methanol in chloroform (5–50%). Alternatively the t-BOC dimer acid may be purified by chromatography on C18 reverse phase silica gel using water and methanol (trifluoroethanol) mixtures.

14.4 Preparation of the t-BOC dimer active ester

The acid from the previous paragraph is converted into the N-hydroxysuccinimidoyl ester or p-nitrophenyl ester by application of the general methods in Example 14.1 and 14.2.

14.5 Preparation of the t-BOC dimer amino acid trifluoro acetate

The t-BOC dimer acid is treated with trifluoro acetic acid as per the general procedure in Example 8.

14.6 Preparation of a t-BOC tetramer acid

The t-BOC dimer active ester and the dimer acid trifluoroacetate are coupled to the t-BOC tetramer acid by the general procedure. Purification is best effected by chromatography on C18 reverse phase silica gel using water and methanol (or trifluoroethanol) mixtures buffered to pH 7.0 with triethylammonium acetate. In this manner chains of substantial length may be prepared by coupling an active ester with a free amine component.

EXAMPLE 15

Geometric assembly of an 8-subunit carbamate-linked polymer

Preparative TLC plates are a product of EM Science purchased from VWR Scientific. HPLC equipment, columns, and supplies are available from Beckman Instruments, Inc. Polypropylene for reverse-phase chromatography is purchased from Polyscience, Inc.: resin-based reverse-phase HPLC columns (PRP-1) are purchased from Hamilton Co. (Reno, Nev.).

The requisite carbamate-linked dimer (0.2 mmol) prepared as described in Example 11, is treated with 4 ml of a 1/1/1 mixture of methanol/THF/glacial acetic acid at rt for 12 h, or preferably 2/1 acetic acid/methanol for 1 h. The solvent is removed under vacuum and the residue is taken up in a minimum of THF. The THF solution is added to a large volume of hexanes and the resulting precipitate is collected and dried. The acetate salt is dissolved in a 4/1 THF/ethanol mixture and DEAE cellulose (0.8 mmol of the base) is added to the vessel. After stirring for 20 min, the heterogeneous mixture is filtered and the filtrate evaporated to dryness. The residue is dissolved in a minimum of 4/1 THF/ethanol and this solution is added to hexanes. The solid is collected and dried. The precipitation procedure is repeated once.

Alternatively. 1 equivalent of toxic acid is added to the deprotection reaction mixture after the reaction is complete. The solution is evaporated. Then the residue is coevaporated three times with 5 ml of DMF. This is used directly in the coupling.

The required N-5'-trityl dimer (0.1 mmol) (as prepared in Example 11) is evaporated twice from DMF, then treated with bis(p-nitrophenyl)carbonate (2 mmol) in the presence of triethylamine (or DMAP or N-methyl imidazole) (catalytic amount) using DMF as the solvent, after 3 h the solvent is evaporated and the residue dissolved in chloroform. This solution is washed twice with 0.01N aqueous NaOH, once with water, then dried over $Na_2SO_4$. The solvent is removed by rotovap and the residue is chromatographed on silica gel eluting with a chloroform/isopropanol (or methanol)/0.1% DMA mixture where the alcohol concentration is adjusted to move the desired product with an $R_f$ of about 0.5. The appropriate fractions are combined and evaporated to dryness. The residue is dissolved in a minimum of THF and this solution is added to an excess of hexanes or hexane/toluene. The precipitated activated dimer is collected by filtration and dried under vacuum.

The 5'-amino dimer nucleoside or its tosylate salt prepared above (0.11 mmol) is twice evaporated from DMF. The activated dimer (0.1 mmol) is added to the reaction vessel and the solids are dissolved in DMF. The solution is concentrated to a small volume and allowed to stand overnight. If the tosylate salt is used, triethylamine (0.3 mmol) is added after the concentration step The solvent is completely removed under vacuum and the resulting residue is dissolved in chloroform. This solution is twice washed with 0.01N aqueous sodium hydroxide, once with water, then dried over sodium sulfate. The solvent is removed by rotovap and the residue is chromatographed on a preparative TLC plate eluting with the appropriate methanol/chloroform/1% triethylamine (or dimethylaniline) solvent system. The band containing the tetramer nucleoside is eluted and the solvent is evaporated. The residue is dissolved in a minimum of THF and this solution is added to hexane or hexane/toluene. The precipitate is collected and dried under vacuum. Alternatively, the oligomer may be chromatographed on silica immediately following removal of DMF, using the same solvent mixtures.

The following transformations are performed using the procedures described above in this example. The requisite N-5'-trityl tetramer nucleoside (0.06 mmol) is treated with 1/1/1 THF/methanol/glacial acetic acid or 2/1 acetic acid/methanol, then purified to afford the 5'-aminotetramer nucleoside. Another aliquot of the N-5'-trityl tetramer nucleoside (0.05 mmol) is activated with bis(p-nitro phenyl)carbonate and subsequently purified. The two tetramers are coupled, worked up, and further purification is achieved either by chromatography on a preparative TLC plate or by HPLC chromatography. The chromatographed material is isolated as a solid, dissolved in a minimum of THF. and then precipitated from hexanes. The octomer nucleoside is collected and dried.

The octamer is configured for further use as follows. The N-5'-trityl octomer nucleoside is treated with 1/1/1 THF/methanol/glacial acetic acid or 2/1 acetic acid/methanol and Purified employing the conditions listed above. The octamer nucleoside (0.01 mmol) is treated with a 1/1 mixture of pyridine/concentrated ammonia (1 ml). Alternatively, base deprotection may be performed prior to detritylation. After standing overnight the solvent is removed by rotovap and the residue is evaporated from ethanol several times. The crude solid is purified using reverse phase (RP-18) HPLC chromatography. The elutants are evaporated and the residue is taken up in DMSO or trifluoroethanol and precipitated from a 1/1 hexane/benzene solvent mixture. The solid is collected and dried.

Generally carbamate-linked polymers containing adenine and cytosine residues comprising at least half of the recognition moieties are soluble in weakly acidic aqueous solution (0.01 to 0.1M acetic acid) while polymers containing guanine (or inosine) and thymine (or uracil) residues comprising at least half of the recognition moieties are soluble in weakly basic aqueous solution (0.01 to 0.1M ammonium hydroxide). Accordingly, any given carbamate-linked polymer (as well as thiocarbamate-linked, amide-linked, and sulfonamide-linked polymers) can be purified by reverse-phase chromatography. Generally the acidic or basic aqueous solvent is mixed to give a column elution gradient ranging from 0% up to about 50% in acetonitrile. The polymer to be purified is dissolved in the aqueous solvent (dilute acetic acid or dilute ammonium hydroxide) and passed onto a suitable reverse-phase column and then the column is eluted with the corresponding acidic or basic aqueous acidic or basic acetonitrile gradient. Generally the shortest fragments elute first, with the desired full-length polymer eluting last. For low to moderate pressure columns, suitable packings are: polyethylene, reverse-phase HPLC grade, and polypropylene, chromatographic. 35μ size from Polysciences, Inc. For HPLC, the polymeric PRP-1 columns from Hamilton Co. are suitable.

EXAMPLE 16

Preparation of a support-bound cleavable linker suitable for stepwise and stepwise/block assembly of carbonate-linked polymers: activation of support and attachment of linker Long-chain alkylamine-derivatized controlled pore glass (Cat. No. 24875) is obtained from Pierce Chemical Co. 2.2-sulfonyldiethanol and dicyclohexylcarbodiimide are obtained from Aldrich Chemical Co.

The amino groups of the glass support (approximately 40 mmol per gram of support) are reacted with succinic anhydride essentially by the method of Matteucci and Caruthers (*J. Amer Chem Soc* (1981) 103:3185) to give free carboxylic acid termini. One-tenth mol of 2,2'-sulfonyldiethanol (60 % by weight in water) is dried by mixing with three volumes of dimethylformamide (DMF), reducing to a thick syrup under vacuum in a warm water bath, adding a second quantity of DMF reducing to a thick syrup, and repeating the process a third time. Dry DMF is then added to give a final sulfonyldiethanol concentration of 2M. A mixture of 1 ml of the sulfonyldiethanol solution plus 0.2 g of dicyclohexylcarbodiimide is added to 1 g of the dry controlled pore glass support carrying carboxylic acid residues and the slurry mixed by rocking or tumbling (not stirring) overnight at rt. Thereafter, the glass support is thoroughly washed with methanol and dried.

When polymers containing linkages which are stable to ammonia (e.g., carbamate-linked, amide-linked polymers) are to be synthesized, the long-chain, alkylamine-derivatized, controlled-pore class need only be reacted with succinic acid, as described above to give a terminal carboxylic acid group.

EXAMPLE 17

Preparation of a 14-subunit carbonate-linked polymer targeted against a conserved sequence in the AIDS viral genome: stepwise assembly on a solid support: addition of the first subunit and chain extension N-methylimidazole and 4-(N,N-dimethylamino) pyridine (DMAP) are obtained from Aldrich Chemical Co. Methyl p-nitrophenyl carbonate is prepared from methyl chloroformate and p-nitrophenol.

The 2'-deoxycytidine subunit(0.1 mmol) prepared as in Example 9 (wherein the N4 carries a p-nitrophenethoxycarbonyl moiety, the 5' oxygen carries a di(p-methoxy)trityl moiety (DMT). and the 3' oxygen carries a p-nitrophenoxycarbonyl moiety) is dissolved in a minimal volume of dry tetrahydrofuran (THF) or dimethylformamide and added to 0.5 g of thoroughly dried controlled pore glass support carrying a linker cleavable by β elimination, prepared as in Example 16. Catalyst (either 1 mmol of N-methylimidazole or 0.1 mmol of DMAP) is introduced and the slurry is mixed by rocking or trembling (not stirring) for 2 hours. The slurry is next filtered, and the solid washed thoroughly with THF.

Any unreacted hydroxyls are capped by adding two ml of THF 1M in methyl p-nitrophenyl carbonate and 0.5M in DMAP and mixing for 20 min at rt. Thereafter, the glass support is washed with THF and filtered.

The dimethoxytrityl at the 5' terminus is then removed by washing the support with dichloromethane followed by treatment with 5 ml of 0.2M dichloroacetic acid in dichloromethane for 5 min at rt. The glass support is next washed with dichloromethane and filtered.

Subsequent subunits, prepared as in Example 1, protected as in Example 2, and activated as in Example 9, are added in a like manner and in the following order: G,A,T,A,A,C,A,T,T, T,T,T,C, (G Protected with the FMOC moiety, A and C Protected with the p-nitrophenethoxy carbonyl moiety).

EXAMPLE 18

Preparation of a 19-subunit carbamate-linked polymer targeted against a conserved sequence in the AIDS viral genome. Stepwise assembly of oligomer blocks on a solid support: addition of the first subunit, chain extension, and cleavage from the support The 5'-amino-2,5'-dideoxycytidine subunit (0.2 mmol). prepared as in Example 3 (wherein the N4 carries a benzoyl moiety the 5'-amine carries a p-methoxytrityl moiety, and the 3' oxygen carries a p-nitrophenoxycarbonyl moiety) is dissolved in a minimal volume of dry THF or DMF and added to 0.5 g of dried controlled pore glass support carrying a cleavable linker, prepared as in Example 16. Catalyst (either 1 mmol N-methylimidazole or 0.1 mmol of DMAP) is introduced and the slurry mixed by rocking or tumbling for 2 h. The slurry is next filtered, and the solid washed thoroughly with THF. Alternatively, the simpler carboxyl-containing support of Example 16 can be mixed with 5'-protected 3'-OH subunit in the presence of DCC coupling agent to link the first subunit to the support via an ester linkage.

The mono-p-methoxy trityl is removed by washing with dichloromethane, followed by treatment with 5 ml of 0.2M dichloroacetic acid in dichloromethane at rt for 1 min. The support is then washed with dichloromethane and filtered. The 5' amino terminus is converted to the free amine form by a brief wash with 3 ml of THF containing 1% by volume of diisopropylethylamine, followed by washing with THF and filtration.

0.1 mmol of 3' p-nitrophenoxycarbonyl activated dimer having the sequence 5'-A-G-3', prepared as in Example 11 (wherein the guanine N2 is protected with an acetyl or phenylacetyl moiety and the adenine N6 is protected with a benzoyl or a p-nitrobenzoyl moiety), is dissolved in a minimal volume of dry THF and added to the glass support and mixing is carried out for 2 h (no catalyst is added for this and subsequent coupling steps). The slurry is next washed with THF and filtered.

Any unreacted amine moieties are capped by adding 2 ml of THF 2M in p-nitrophenyl acetate and mixing at rt for 20 min. Thereafter, the glass support is washed with THF and filtered.

The mono-methoxytrityl at the 5' terminus is removed with dichloroacetic acid, as before.

Subsequent activated dimeric subunits prepared as in Example 15 (wherein the exocyclic ring nitrogen of cytosine is protected with a benzoyl moiety and the exocyclic ring nitrogen of A is protected with a benzoyl or a p-nitrobenzoyl moiety), and added in a like manner and in the following order: A-T, C-A, T-A, T-T, T-T, A-C, A-C, C-A (5' to 3').

Subunits having base exocyclic ring nitrogen protective groups removable by strong nonnucleophilic bases (e.g., p-nitrophenethoxycarbonyl or phenylsulfonyl ethoxycarbonyl for A and C, and FMOC for G) can also be used for assembling polymers by the procedure above. However, polymers having these alternative protective groups are generally deprotected by treatment with DBU (1,8-diazobicyclo[5.4.0]undec-7-ene) rather than by ammonium hydroxide.

The polymer is cleaved from the support using DBU (for the β-elimination cleavable linker) or NH₄OH (when bound to the support via an ester linkage) and base-protective groups are removed in 55° C. DMSO/-conNH₄OH (55° C.) 1:1 by volume or in 55° C. 1,2- propanediol/conNH₄OH 1:1 by vol. Purification of the deprotected polymer is as in Example 15. The terminal trityl group can be removed before or after cleavage from the support, or after purification via reverse-phase chromatography.

EXAMPLE 19

Preparation of a 19-subunit amide-linked polymer targeted against a conserved sequence in the AIDS viral genome. Stepwise assembly of oligomer blocks on a solid support: addition of the first subunit and chain extension A cytosine-containing acyclic-backboned subunit (0.2 mmol). prepared as in Example 14 (wherein the N4 of the cytosine carries a 2(P-nitrophenyl)ethoxycarbonyl moiety, the amine of the backbone carries a t-butoxycarbonyl moiety, and the carboxyl is in the form of a p-nitrophenyl ester) is dissolved in a minimal volume of dry THF and added to 0.5 g of dried controlled pore glass support carrying a linker cleavable by $\beta$-elimination, prepared as in Example 16. Catalyst (either 1 mmol of N-methylimidazole or 0.1 mmol of DMAP) is introduced and the support mixed for 2 h, filtered, and the solid is washed thoroughly with THF. Alternatively, subunit having a free carboxylic acid can simply be mixed with the support in the presence of dicyclohexylcarbodiimide.

The t-BOC is removed by washing the support with dichloromethane followed by treatment at rt with 5 ml of 20% by volume trifluoroacetic acid in methylene chloride for 30 min. The support is washed with dichloromethane and filtered. The support-bound amino terminus is converted to the free amine form by a brief wash with 3 ml of THF containing 1% by volume of diisopropylethylamine, followed by a THF wash.

The activated dimeric subunit (0.1 mmol) having the sequence (C-terminus)-G-A-(N-terminus) prepared as in Example 14 (wherein the N2 of guanine carries an FMOC moiety, the N6 of adenine carries a p-nitrophenethoxycarbonyl moiety, the backbone amino terminus carries a t-BOC moiety, and the carboxy terminus is in the form of a p-nitrophenyl ester) is dissolved in a minimal volume of dry THF and added to the glass support and mixing is carried out for 2 h (no catalyst is added for this or subsequent coupling steps). The support is washed with THF.

Any unreacted amine moieties are capped by adding 2 ml of 2M p-nitrophenyl acetate in THF and mixing at rt for 20 min or by adding acetic anhydride plus a catalytic amount of hydroxybenztriazole. Thereafter, the glass support is washed with THF.

The terminal t-BOC moiety is removed with TFA and the support neutralized, as described above.

Subsequent dimeric subunits, prepared as in Example 14, are added in a like manner in the following order: (C-terminus) T-A, A-C, A-T, T-T, T-T, C-A, C-A, A-C (N-terminus).

Subunits having exocyclic ring nitrogen protective groups removable by good nucleophiles (e.g., benzoyl for C, benzoyl or nitrobenzoyl for A, and acetyl, phenylacetyl, or isobutyryl for G) can also be used for assembling polymers by the above procedures. However, polymers having these alternative protective groups are generally deprotected by treatment with ammonium hydroxide rather than by DBU.

The amide-linked polymer is cleaved from the support, deprotected, and purified as in Example 18.

EXAMPLE 20

Attachment of carbonate-linked polymer to a solid support through a linker arm 20.1 Preparation of a bifunctional hexane linker arm Dowex 50X pyridinium resin is obtained from Bio-Rad (Richmond, Calif.), and 6-aminohexanol, dimethylformamide and 3-hydroxypropanenitrile are obtained from commercial sources. 6-(2-methylsulfonyl)-ethyl p-nitrophenyl carbonate is prepared according to Eberle, et al., *Helvetica Chimica Acta* (1975) 58:2106.

A bifunctional hexane linker arm 6-(2-(methylsulfonyl)-ethoxycarbonylamino)-hexanol is prepared by reacting 6-aminohexanol (1 mmol) with 2-(methylsulfonyl) ethyl p-nitrophenylcarbonate (1 mmol) in 1 ml dimethylformamide for up to 4 hours at 25° C. The reaction mixture is poured into water, extracted thoroughly with benzene, the benzene washed with water, and the organic solvent then dried with sodium sulfate and evaporated to give the carbamate alcohol, which is purified by silica gel chromatography using a methanol/chloroform solvent mixture. This is activated with bis(p-nitrophenyl) carbonate in DMF with a catalytic amount of triethylamine, and purified by silica gel chromatography.

20.2 Preparation of carbonate-linked polymer with a 5'-O-(6-aminohexyl) linker arm The fully-protected carbonate-linked support-bound polymer of Example 17 is detritylated by the standard method and then contacted with a 10-fold molar excess of the above activated linker arm in the presence of N-methylimidazole or 4(N,N-dimethylamino) pyridine catalyst. This derivatized polymer is cleaved from the support and the bases are deprotected with stringently anhydrous DMSO using DBU (1,8-diazabicyclo [5.4.0]undec-7-7-ene) (from Aldrich). The DBU is removed by repeatedly precipitating the polymer from dry DMSO with dry ether. Before the final ether precipitation, a trace of acetic acid is added to neutralize any residual DBU.

20.3 Attachment of 5'-O-(aminohexylcarbonate-linked polymer to a solid support

One g of cellulose (20μ particle size from Sigma Chemical Co. ) is reacted with an equal weight of bis(p-nitrophenyl)carbonate in 20 ml of acetonitrile plus 1 ml of triethylamine for 4 h at rt. The cellulose is filtered, thoroughly washed with 3 portions of acetonitrile, and dried overnight under high vacuum.

Ten μmol of polymer prepared as above (Example 20.2) is suspended in 1 ml of DMSO containing 0.1% triethylamine and then 0.1 g of the activated cellulose is added and the slurry gently rocked for 6 h at rt, filtered, thoroughly washed with 0.1N aqueous ammonium acetate, and then dried.

EXAMPLE 21

Preparation of the Reagent Support 21.1 Aminomethylated polystyrene is prepared as described by B. A. Mukhitdinova, E. E. Eighozin, and G. A. Makhmudova, *Izv Akad Nauk Kaz SSR., Ser Khim* (1980) 48. Disuccinimido dicarbonate and 6-aminohexanol are obtained from Aldrich.

Aminomethylated polystyrene (1 g, 3.0 meq/g) is suspended in water/acetonitrile (10 ml. 3:1 v/v) and treated with succinic anhydride (20 mmol) at 4° C. The pH of the solution is kept at 8.0 by the addition of 20% NaOH. When the pH of the solution holds constant, the reaction is continued for 24 hours. The beads are filtered, washed with 2N HCl, water (until the pH of the washings is neutral) and made anhydrous by repeated washings with dioxane.

The support (having bound acid groups) from the previous paragraph is reacted with disuccinimido carbonate (20 mmol) in acetonitrile (10 ml) for 24 hours at 25° C. The support is isolated by filtration and the support having bound succinimido ester is washed thoroughly with acetonitrile.

The support from above is suspended in dimethylformamide (10 ml) and reacted with 6-aminohexanol (20 mmol) for 24 hours at 25° C. The support is isolated by filtration and the support having the bound alcohol chain is washed thoroughly with dimethylformamide.

21.2 Alternative preparation of reagent support

One g of the activated cellulose support of Example 20.3 is added to 10 ml of DMSO containing 1 g of triglycine (Sigma Chemical Co.) plus 1 ml of diisopropylethylamine and the slurry rocked gently for 2 h at rt. One ml of NH$_4$OH is next added, and stirring is continued for 30 min. The cellulose is filtered washed with DMSO, then with dry DMF and the cellulose with bound linker is dried under high vacuum overnight.

EXAMPLE 22

Procedures for coupling amine-terminated polymers to supports

Supports containing linker arms terminating in a hydroxyl moiety prepared as in Example 21.1. are activated with an excess of carbonyl diimidazole in DMF or with an excess of bis(p-nitrophenyl)carbonate plus a catalytic amount of triethylamine or N-methylimidazole in DMF. The activated support is washed thoroughly with dry DMF and then 100 mg of the activated support is added to 1 ml of DMSO containing 10 μmole of purified amine-terminated polymer (prepared as in Examples 18, 19, or 20.2) plus 0.1 ml of diisopropylethylamine. The slurry is gently rocked for 4 h at rt. The support material is washed briefly with 0.1N aqueous NH$_4$OH, then repeatedly with distilled water, and finally the resultant diagnostic reagent is dried overnight under vacuum.

Supports containing linker arms terminating in a carboxylic acid moiety, prepared as in Example 21.2. are activated with DCC (dicyclohexylcarbodiimide) plus p-nitrophenol in DMF. The activated support is washed thoroughly with dry DMF, then reacted with amine-terminated polymers as described above.

EXAMPLE 23

Protection of the Amino Group as the BOC-derivative 4-(N-tert-butoxycarbonyl-N-methylamino)-butyric Acid 4-(Methylamino)-butyric acid is obtained from Aldrich. Di-tert-butyl dicarbonate is obtained from Pierce (Rockford, Ill.).

4-(methylamino)-butyric acid (10 mmol) is dissolved in dioxane/water (30 ml, 2/1) and 1N NaOH (10 ml) is added. The solution is cooled to 0° C. and di-tert-butyl carbonate (11 mmol) is added with stirring. After 30 minutes at 25° C. the dioxane is removed under reduced pressure and the pH of the solution is adjusted to pH-2.5 by the addition of potassium bisulfate. The aqueous phase is thoroughly extracted with ethyl acetate and the organic layers combined and dried over sodium sulfate. Removal of the solvents under reduced pressure gives the free acid which is purified by recrystallization from chloroform/hexane, or by chromatography on silica gel using chloroform/methanol mixtures.

EXAMPLE 24

Introduction of the Terminal Dimethylamino Group and General Procedure for the Activation of the Acid by Conversion to the Imidazolide and General Procedure for Coupling with an Amine N,N'-carbonyl diimidazole is obtained from Aldrich.

A solution of the BOC-protected amino acid (or oligopeptide acid, 1 mmol) is treated with carbonyl diimidazole (1 mmol) at −20° C. for 6 hours. At this time, a solution of dimethylamine (excess) or oligopeptide amine (1 mmol) prepared as in Example 25, in DMF (1 ml) is added at −20° C. and the reaction then stirred at 25° C. for 12 hours. The solvent is removed by reduced pressure and the residue is chromatographed on silica gel using methanol/chloroform to give N,N-dimethyl 4-(N-tert-butoxycarbonyl-N-methylamino)-butyramide.

EXAMPLE 25

General procedure for the Removal of the BOC-protecting Group of N,N-Dimethyl 4-(methylamino)-butyramide Trifluoroacetic acid is obtained from Aldrich.

N,N-Dimethyl 4-(N-tert-butoxycarbonyl N-methylamino)-butyramide (of BOC-protected oligopeptide 1 mmol) (Example 24) is dissolved in trifluoroacetic acid (5 ml) and stirred for 1 hour at 25° C. The solvent is removed and the residue is partitioned between 1N NaOH/saturated NaCl (1/10) and chloroform. The aqueous phase was thoroughly extracted with chloroform and the combined organic layers were dried over sodium sulfate and evaporated under reduced pressure to give the free amine. This can be used directly for further coupling reactions, or can be purified on silica gel using methanol/chloroform mixtures containing 1% triethylamine.

Using the coupling procedure and the BOC deprotection sequence, polyamides of various lengths may be prepared. For example, reaction of 4-(N-tert-butoxycarbonyl-N-methylamino)-butyryl imidazolide with N,N-dimethyl 4-(methylamino)-butyramide produces the dimeric monoamide. Removal of the BOC group and coupling with another equivalent of the imidazolide produces the trimeric diamide the process being repeated until the desired length is achieved.

Alternatively, 4-(N-tert-butoxycarbonyl-N-methylamino)-butyryl imidazolide is reacted with 4-(methylamino)-butyric acid and the resulting dimeric acid is activated with N,N-carbonyl diimidazole and coupled with free amino oligoamides.

EXAMPLE 26

General Procedure for the Reduction of the Amide Linkages to Amines

AG-50 and Dowex-50W are obtained from Bio-Rad (Richmond, Calif.).

The oligomeric polyamide to be reduced is treated with trifluoroacetic acid as in the general procedure in order to remove the BOC group. After isolation and purification, the free amine (1 mmol) in tetrahydrofuran (1 ml) is added dropwise to a solution of borane (2 mmol per amide residue) in tetrahydrofuran (3 ml) at 25° C. The solution is refluxed for 1 hour cooled to 0° C. and treated dropwise with 12N HCl (2 ml). After all evolution of gas has ceased, the solution is evaporated under reduced pressure to remove the tetrahydrofuran, and the remaining aqueous solution is applied to an AG-50 ion exchange resin and purified by washing the column of water (10 ml) and eluting the polyamine with a buffer comprised of sodium acetate (0.1-2.0M) and sodium chloride (0.1-2.0M) at pH 5. After collection and evaporation of the fractions containing the desired product, the residue is dissolved in 1N HCl (4 ml) and applied to a Dowex 50W ion exchange column. After washing with water, and then 2M HCl, the product is recovered as the hydrochloride by elution with 6N HCl and removal of the solvent under reduced pressure.

If desired, the primary amino group of the polyamine can be protected as the BOC-derivative and the remaining tertiary amine moieties converted to the quaternary ammonium salt using methyl iodide as per Example 28.

EXAMPLE 27

General procedure for the Incorporation of a Terminal Primary Amino Group into the Polyamine 4-aminobutyric acid is converted to the BOC-derivative. This is reacted with carbonyl diimidazole as in Example 24 and treated with the dimeric amide from Example 25. Cleavage of the BOC-group and reduction as in Example 26 produced the polyamine.

If desired, the primary amino group of the polyamine can be protected as the BOC-derivative as in the general procedure and converted into the ammonium salt using methyl iodide as per Example 28.

EXAMPLE 28

General Method for the Conversion of the Polyamine to the Poly (quaternary ammonium) Salt (3-aminopropyl-)dimethyl-(3-(5'-dimethylamino-1-naphthalene sulfonylamino)-propyl)-ammonium chloride Methyl iodide and ethyldiisopropylamine are obtained from Aldrich.

To a solution of bis-(3-aminopropyl) methylamine (1 mmol) in dioxane/water (3 ml, 2/1) is added 1N NaOH (1 ml). With stirring, at 0° C. is added di-tert-butyl dicarbonate (1.1 mmol) and the mixture is stirred at 25° C. for 30 minutes. The basic solution is thoroughly extracted with chloroform and the combined organic layers are dried over sodium sulfate and evaporated. The product is dried by evaporation from anhydrous dimethylformamide (5 ml). The residue is dissolved in DMF and the solution treated with methyl iodide (12 mmol) at 25° C. for 1 hour. The solvent is evaporated and the residue is dissolved in trifluoroacetic acid (5 ml). After 1 hour, the solvent is evaporated and the residue dissolved in pyridine (5 ml). To this solution is added ethyldiisopropylamine (2 mmol per mmol of primary, secondary, and tertiary amine function) and the dansyl group is introduced by treatment of the solution with 5-dimethylaminonaphthalene-sulfonyl chloride (0.9 mmol) (obtained as in Example XX) at 0° C., then allowing the mixture to stand overnight at 4° C. The reaction product is purified as in the previous paragraph by ion exchange chromatography and isolated as the hydrochloride salt.

Alternatively, the dansylated reporter may be treated directly with methyl iodide in dimethylformamide and purified by ion exchange chromatography, as above.

EXAMPLE 29

General Method for the Introduction of the Fluorophore 29.1 5-Dimethylamino-1-naphthalene-sulfonyl chloride is obtained from Aldrich.

To a solution of a starting polyamine-prepared as in Example 27 or 28 (1 mmol) in pyridine (5 ml) at 0° C. is added 5-dimethylamino-1-naphthalene-sulfonyl chloride (0.85 mmol) and the mixture is stirred overnight at 4° C. The pyridine is then removed at 25° C. under reduced pressure and the residue dissolved in 1N HCl (5 ml) and applied to an AG-50W ion exchange column. After washing with water (10 ml), the product is eluted with a buffer comprised of sodium acetate (0.1-2.0M) and sodium chloride (0.1-2.0M) at pH 5. After collecting and concentrating the fractions containing the product, the residue is dissolved in water (10 ml) and applied to a Dowex 50-W (Bio-Rad) ion exchange column and washed with water (10 ml), 0.5N HCl (5 ml), and finally the product is eluted with 6N HCl. The hydrochloride salt of the product is obtained by removal of the solvent under reduced pressure.

29.2 Simplified method for preparation of dicationic and tricationic fluorescent reporters To a solution of triamine (spermidine or 3.3'-diamine-N-methyldipropylamine) or tetramine (spermine or N,N'-bis(3-aminopropyl)-1,3-propanediamine) (2 mmol) in pyridine (10 ml) at 0° C. is added -dimethylamine-1-naphthalene-sulfonylchloride (1 mmol) and the mixture is stirred overnight at rt. The reaction mixture is worked up as above (29.1).

EXAMPLE 30

Preparation of Enzymatic Reporter

A polycationic tail having a primary amine at one terminus is prepared as described in Example 27. giving the structure:

One mmol of this product is reacted for 24 hr at room temperature in the dark with an excess of 4-fluoro-3-nitro-phenylazide in low light conditions, the solvent is removed under reduced pressure, and the solid is triturated with hexane to remove unreacted phenylazide. The solid is next suspended in 10 ml of 0.1M NaCl and cacodylic acid is added to lower the pH to 7.2. Next. 5 mg of alkaline phosphatase (Sigma Chem Co., #P5778) is added to 1 ml of the foregoing tail solution and illuminated for 1 hr with a high flux of 366 nm light. The resulting reporter is dialyzed for 18 hr against a large volume of buffer (0.1M NaCl, 0.05M sodium cacodylate, pH 7.0) to remove cationic tail not linked to the enzyme. Bovine serum albumin (1% w/v) and sodium azide (0.02% w/v) are added to stabilize and preserve the enzyme moiety of this hexacationic reporter. Storage of this reporter solution is at 4° C. in the dark.

EXAMPLE 31

Preparation of Diagnostic Reagent for Detection of Herpes Simplex, Types I and II

31.1 Preparation

The 16-base sequence at positions 462 to 477 of the 2gD gene of Herpes simplex virus, types I and II. '-GCGGGGCTGCGTTCGG-3', comprises the selected target sequence (Lasky & Downbenko, *DNA* (1984) 3:23). A complementary reagent polymer composed of carbamate-linked subunits is constructed substantially according to the methods of Example 18.

The purified polymer is coupled to an Affi-Gel 10 solid support material, by conventional coupling methods, or is coupled to a cellulose support as in Example 22.2.

31.2 Assessment of target binding affinity

The melting temperature of the polymer/analyte duplex is determined using a synthetic oligonucleotide having the 5'-GCGGGGCTGCGTTCGG-3' target sequence. This target sequence, which is purchased, or constructed by conventional methods, is mixed with a substantially equimolar amount of the polymer (before polymer attachment to the solid support) in annealing buffer (10 mM EDTA, 100 mM sodium phosphate, pH 7.2). This solution is heated to 90° C. and slowly cooled to room temperature to effect annealing. The temperature is slowly raised and absorbance is recorded as a function of the temperature. The melting temperature (Tm) is taken as the temperature at which half the total absorbance change has occurred.

31.3 Detection of Herpes Simplex, Types I and II

An analyte sample, taken as a skin scrape of an infected area, is suspended in 0.1 ml of EDTA-detergent solution (10 mM EDTA. 1% w/v sodium dodecyl sulfate, pH to 7.0), homogenized briefly in a micro tissue grinder (Kontes #K-885470) and the homogenate filtered centrifugally in a microfilter (VWR Scientific #28151-807). One-half ml of 4.5M sodium trichloroacetate is added, followed in a few seconds by 0.6 ml of ethanol. This preparation is placed on ice for 30 min and then centrifuged for 5 min at 10,000 g. The supernatant is carefully decanted and discarded and the tube is gently rinsed with aqueous 80% ethanol. The pelleted material (often not visible) is resuspended in 0.05 ml of annealing buffer (10 mM EDTA, 100 mM sodium phosphate, pH 7.2) and added to an appropriate amount of diagnostic reagent (estimated reagent polymer/analyte molar ratio > 100). Annealing is carried out at a temperature 8° C. below the Tm of the polymer/target duplex (predetermined as described in Example 31.2) for 30 min and then the diaqnostic reagent is washed three times with 2 ml volumes of annealing buffer. This washing is conveniently carried out centrifugally in a microfilter. After washing the diagnostic reagent is suspended in 0.2 ml of reporter solution containing 1 mg of a tricationic fluorescent reporter prepared as described in Example 29.1 or 29.2. The reporter solution is buffered with 0.1N phosphate, NaOH, to pH 7.2. The diagnostic reagent is next washed three times with 2 ml volumes of reporter-free buffer solution. Finally, reporter is eluted from the diagnostic reagent with 0.1 ml of 2M NaCl and the elutant assessed for fluorescence in a spectrofluorometer. The fluorescence from a control sample lacking analyte is subtracted to provide a quantitative measure proportional to the analyte present in the initial sample. Alternatively, the reporter can be assessed while still bound to the diagnostic reagent/analyte complex.

EXAMPLE 32

Preparation and Use of a Diagnostic Reagent for Detection of the AIDS Virus

32.1 Preparation

The 16-base sequence at positions 8441-8456 of the ORF-2 gene of AIDS-associated retrovirus (ARV-2), 5'-GATGGGGTGGGAGCAG-3', comprises the selected target sequence (Sanchez-Pescador, et al, *Science* (1985) 227:484). A complementary polymer having carbamate-linked subunits is constructed substantially according to methods detailed in Example 18. Briefly, the 2' deoxyribonucleosides dA, dC, and dG are protected as in Example 2. These protected nucleosides plus thymidine are then converted to their 5' amino derivatives. Polymeric support is prepared, and subunits are linked sequentially to this support by the method described in Examples 18 to give a support-bound protected polymer having the sequence: Support-CTACC CCACCCTCGTC-5'. In the final step the base-protective groups are removed to give the desired carbamate-linked diagnostic reagent free in solution. This is next purified as in Example 18 and linked to a solid support as in Example 22.

32.2 Assessment of target binding affinity

The melting temperature of the polymer/analyte is determined as follows. An RNA transcript is prepared from single-stranded polynucleotide containing a sequence complementary to the target sequence. This target-containing RNA is suspended in annealing buffer (10 mM EDTA, 100 mM sodium phosphate pH 7.0) and added to the above diagnostic reagent. The mixture is warmed to 90° C. and slowly cooled to room temperature to effect annealing. Subsequently the diagnostic reagent is placed in a small water-jacketed chromatography column through which annealing buffer is slowly pumped. The temperature is slowly raised while monitoring the effluent for released RNA. The release temperature (Tr) is the temperature at which the RNA is eluted from the column. This Tr value often differs by one to a few degrees C from the corresponding Tm determined by the hyperchromic shift method described in Example 31.

32.3 Detection of AIDS Virus

Two ml of blood suspected of containing AIDS viral sequences is added to 8 ml of 4.5M sodium trichloroacetate containing 0.1 mg polyadenylic acid (Sigma Chem Co #P9403). After a few seconds 10 ml of ethanol is added and the preparation chilled for 30 min in an ice bath and then centrifuged for 5 min at 10,000 g. The supernatant is carefully decanted and discarded. The pelleted nucleic acid (often not visible) is washed with aqueous 80% ethanol, drained well, and resuspended in 0.1 ml of annealing buffer (10 mM EDTA, 100 mM sodium phosphate, pH 7.2) and added to an appropriate amount of diagnostic reagent from Example 32.1 (estimated polymer/target molar ratio > 100). Annealing is carried out at a temperature 7° C. below the Tr of the polymer/target duplex (predetermined as in Example 32.2) for one hr and then the diagnostic reagent is washed three times with 2 ml volumes of annealing buffer. This washing is conveniently carried out centrifugally in a microfilter.

After washing, the diagnostic reagent is suspended in 0.2 ml of an enzymatic-hexacationic reporter solution prepared as in Example 30. After 30 sec the diagnostic reagent is washed three times with 2 ml volumes of reporter-free wash solution. Thereafter, the diagnostic reagent is suspended in developing solution (15 mM p-nitrophenyl phosphate, 0.5 mM MgCl, 1.0M diethanolamine, pH 9.8) and incubated for 3 hr at 37° C. Reporter-generated p-nitrophenol is quantitated spectrophotometrically. Corresponding absorbance from a control sample lacking analyte is subtracted to provide a quantitative measure proportional to the analyte present in the initial sample.

While the invention has been described with reference to particular embodiments, it will be appreciated that various changes and modifications can be made without departing from the invention. For example, the diagnostic reagent may include multiple species of support-bound polymers, each specie designed to bind to a different selected target sequence in polynucleotide strands from different analytes, or the diagnostic reagent may include two species of support-bound polymers, with each specie designed to bind to a different complementary strand of a duplex analyte. These multi-specie reagents offer the potential of detecting more than one analyte in a diagnostic test, or of doubling the sensitivity of detection of a single duplex analyte.

What is claimed is:

1. A diagnostic system for determination of a single-stranded polynucleotide analyte containing a selected heteromeric target sequence of bases, said system comprising:

a diagnostic reagent composed of a solid support, and attached to the solid support, multiple polymer molecules, each composed of a heteromeric sequence of base-complementary recognition moieties selected from the group consisting of purine and pyrimidine heterocycles adapted to hydrogen-bond to corresponding, contiguous bases in the target sequence, under selected binding conditions, and an unbranched, substantially uncharged backbone, composed of subunit backbone moieties, supporting the recognition moieties at positions which allow hydrogen bonding between the recognition moieties and the corresponding bases in the target sequence, where the subunit backbone moieties are chosen from a group consisting of cyclic moieties, of 5 to 7 atoms in length, and acyclic moieties, of 4 to 6 atoms in length; and, molecules of a reporter, where said reporter is composed of an oligocationic tail adapted to bind electrostatically to the charged backbone of the polynucleotide analyte, and attached to the tail, one or more reporter groups adapted to produce a signal by which the presence of the reporter can be detected.

2. The system of claim 1, wherein the polymer molecules have the form:

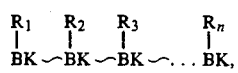

where:

(a) where $R_1$-$R_n$ are recognition moieties selected from purine, and pyrimidine heterocycles effective to bind by Watson/Crick pairing to corresponding, contiguous bases in the target sequence, and Bk are backbone moieties;

(b) n is such that the total number of Watson/Crick hydrogen bonds formed between a polymer molecule and target sequence is at least 12;

(c) the backbone moiety length ranges from 5 to 7 atoms if the backbone moieties have a cyclic structure, and 4 to 6 atoms if the backbone moieties have an acyclic structure; and (d) the backbone moieties support the recognition moieties at positions which allow Watson/Crick base pairing between the recognition moieties and the corresponding, contiguous bases of the target sequences.

3. The system of claim 2, wherein the recognition moieties are selected from the following group:

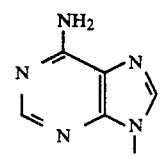  1.

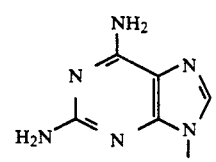  2.

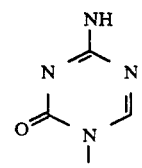  3.

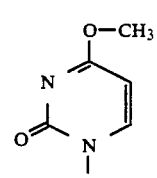  4.

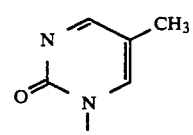  5.

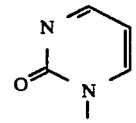  6.

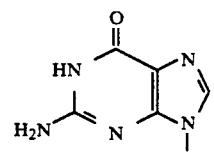  7.

-continued

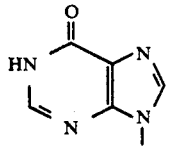

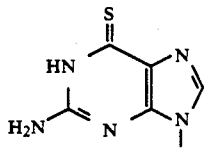

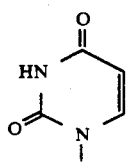

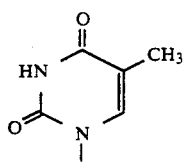

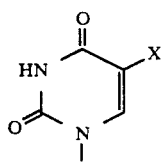

where X=F, CL, Br, or I.

4. The system of claim 2, wherein Bk is a cyclic moiety and Bk≈Bk are backbone moieties joined predominantly by chemically stable, uncharged, achiral linkages having one of the following forms:

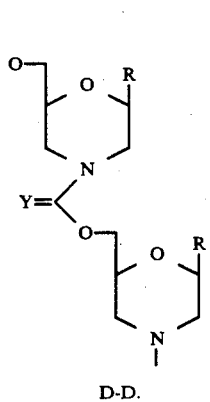
D-D.

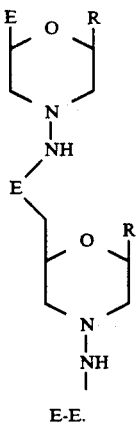
E-E.

where Y=O, S and

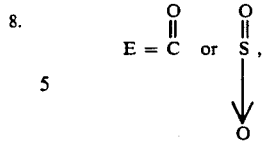

and R is a selected recognition moiety.

5. The system of claim 2, wherein BK is an acyclic moiety and BK~BK are backbone moieties joined predominantly by chemically stable, uncharged, achiral linkages having one of the following forms:

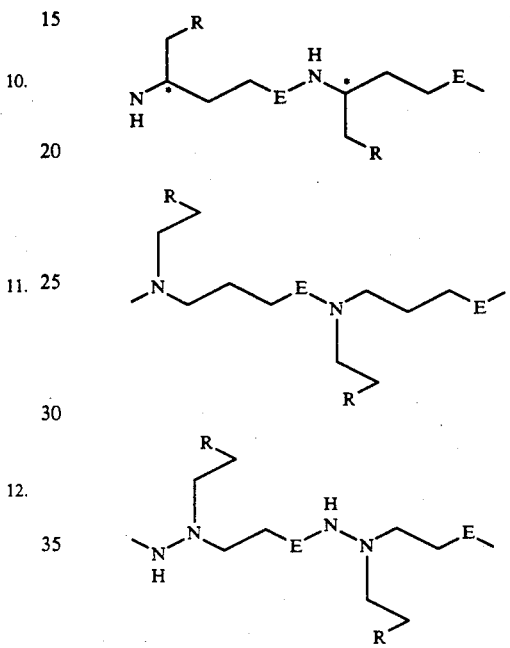

where

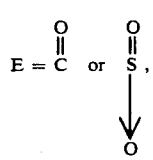

and R is a selected recognition moiety.

6. The system of claim 1, wherein the tail in the reporter contains positive groups at intervals whose spacing corresponds approximately to the spacing between adjacent phosphate groups in the backbone of the polynucleotide analyte.

7. The system of claim 6, wherein the tail contains an oligocationic portion having the formula:

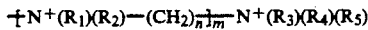

where n=2-5, m>0, and each $R_1$–$R_5$=H or alkyl group.

8. The system of claim 7, wherein the reporter group in the reporter includes one or more fluorescent, chromophore, enzyme, or radioisotope groups.

9. A method for determination of a polynucleotide analyte containing a selected target base sequence, said method comprising providing a diagnostic reagent composed of a solid support and, attached to the support, multiple polymer molecules, each composed of a heteromeric sequence of base-complementary recognition moieties selected from the group consisting of purine and pyrimidine heterocycles effective to hydrogen-bond to corresponding, contiguous bases in the target sequence, under selected binding conditions, and an unbranched, substantially uncharged, substantially stereoregular backbone, composed of subunit backbone moieties, supporting the recognition moieties at positions which allow hydrogen bonding between the moieties and the corresponding bases in the target sequence, where the subunit backbone moieties are chosen from the group consisting of cyclic moieties, of 5 to 7 atoms in length, and acyclic moieties, of 4 to 6 atoms in length; and, mixing the reagent and an analyte-containing sample under such selected conditions, to produce sequence-specific binding of the analyte to the reagent polymers, providing a reporter composed of an oligocationic tail adapted to bind electrostatically to the charged backbone of the polynucleotide analyte, and attached to the tail, one or more reporter groups adapted to produce a signal by which the presence of the reporter can be detected, binding the reporter to analyte which has bound by sequence-specific binding to the reagent, and determining the extent of reporter binding to the analyte.

10. The method of claim 9, for use in determination of a duplex nucleic acid analyte, wherein said mixing is performed at a selected ionic strength of less than about 0.2M monovalent cation, in the presence of a divalent cation chelating agent and at a temperature above the melting temperature of such duplex analyte.

11. The system of claim 1, wherein the backbone of the polymer molecule is substantially stereoregular.

* * * * *